United States Patent [19]

Tatsuoka et al.

[11] Patent Number: 4,713,453

[45] Date of Patent: Dec. 15, 1987

[54] OXABICYCLOHEPTANE DERIVATIVES

[75] Inventors: Toshio Tatsuoka, Hyogo; Kenji Suzuki, Osaka; Kayoko Imao, Nara; Fumio Satoh, Kyoto; Seiji Miyano; Kunihiro Sumoto, both of Fukuoka, all of Japan

[73] Assignee: Suntori Limited, Osaka, Japan

[21] Appl. No.: 19,973

[22] Filed: Feb. 27, 1987

[30] Foreign Application Priority Data

Feb. 27, 1986 [JP] Japan ............................. 61-42732

[51] Int. Cl.$^4$ .................. C07D 417/00; C07D 413/00; C07D 405/00; C07D 401/00
[52] U.S. Cl. ......................... 544/60; 544/146; 544/150; 544/375; 546/196; 548/336; 548/525; 549/60; 549/385; 549/395; 514/222; 514/231; 514/326; 514/444; 514/454; 514/455
[58] Field of Search ................ 549/60, 385, 395; 544/146, 150, 375, 60; 548/525, 336; 546/196

[56] References Cited

U.S. PATENT DOCUMENTS 3,468,897  9/1969  Fournari ..................... 549/60
4,545,993 10/1985  Okamoto ..................... 549/60

Primary Examiner—Alan Siegel
Attorney, Agent, or Firm—Cushman, Darby & Cushman

[57] ABSTRACT

The present invention relates to a novel oxabicycloheptane derivative of the following formula and a pharmaceutically acceptable salt thereof:

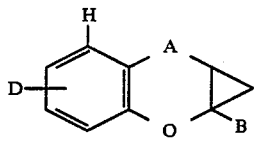

where D is a hydrogen atom, a halogen atom, a hydroxyl group, an alkoxy group, an arylalkoxy group, an acyloxy group, a dialkylcarbamoyloxy group or an amidoalkyloxy group; B is a substituted or unsubstituted phenyl, thienyl or furyl group; /A\ is the group

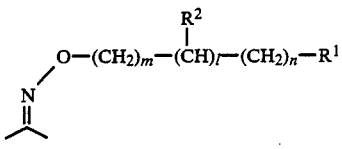

(where l is 0 or 1; m and n are each 1 or more, provided that m+n is an interger of 2-8; $R^1$ is an alkylamino group, a dialkylamino group, an arylalkylamino group, a morpholino group, a thiomorpholino group, a 1-pyrrolidinyl group, a piperidino group, an N-alkylpiperazinyl group, an N-hydroxyalkylpiperazinyl or a pyrrolizidinyl group; and $R^2$ is a lower alkyl group or a hydroxl group), or the group

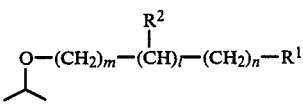

(where l, m, n, $R^1$ and $R^2$ are each the same as defined above), or the group

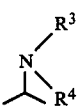

(where $R^3$ and $R^4$ which may be the same or different each represents a hydrogen atom, a lower alkyl group, an alkoxycarbonyl group or an acyl group), or the group

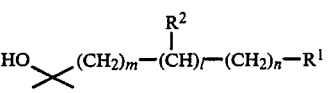

(where m, l, n, $R^1$ and $R^2$ are each the same as defined above).

The oxabicycloheptane derivative having the formula defined above and pharmaceutically acceptable salts thereof are effective in ameliorating or eliminating the symptoms that appear either as a result of organic disorders in the brain or on account of pathergasia. These compouds also have antidepressant effects and the useful as psychopharmaceuticals.

5 Claims, No Drawings

OXABICYCLOHEPTANE DERIVATIVES

BACKGROUND OF THE INVENTION

The present invention relates to a novel oxabicycloheptane derivative of the following formula and a pharmaceutically acceptable salt thereof:

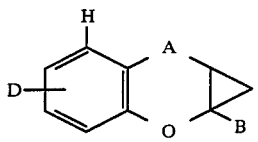

where D is a hydrogen atom, a halogen atom, a hydroxyl group, and alkoxy group, an arylalkoxy group, an acyloxy group, a dialkylcarbamoyloxy group or an amidoalkyloxy group; B is a substituted or unsubstituted phenyl, thienyl or furyl group; $\diagup\!\!\!A\!\!\!\diagdown$ is the group

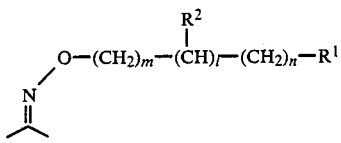

(where l is 0 or 1; m and n are each 1 or more, provided that m+n is an integer of 2-8; $R^1$ is an alkylamino group, a dialkylamino group, an arylalkylamino group, a morpholino group, a thiomorpholino group, a 1-pyrrolidinyl group, a piperidino group, an N-alkylpiperazinyl group, an N-hydroxyalkylpiperazinyl or a pyrrolizidinyl group; and $R^2$ is a lower alkyl group or a hydroxy group), or the group

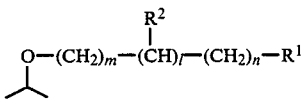

(where l, m, n, $R^1$ and $R^2$ are each the same as defined above), or the group

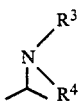

(where $R^3$ and $R^4$ which may be the same or different each represents a hydrogen atom, a lower alkyl group, an alkoxycarbonyl group or an acyl group), or the group

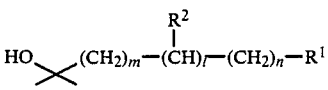

(where m, l, n, $R^1$ and $R^2$ are each the same as defined above).

The oxabicycloheptane derivative having the formula defined above and pharmaceutically acceptable salts thereof are effective in ameliorating or eliminating the symptoms that appear either as a result of organic disorders in the brain or on account of pathergasia. These compounds also have antidepressant effects and are useful as psychopharmaceuticals.

The term "organic disorders in the brain" as used hereinabove means symptoms resulting from cerebral ischemic disorders such as the sequelae of cerebral infarct, encephalorrhagia and cerebroarteriosclerosis, as well as various organic disorders resulting from senile dementia, dementia presenilis, amnesia, and the sequelae of traumas or operations on the brain. The term "pathergasia" means diseases on psychic functions resulting from mania, depression, neurosis, Parkinson's disease, schizophrenia and schizophrenic disorders, chorea, as well as those resulting from use of drugs and alcohol.

Brain cells maintain an intracellular environment that entirely differs from their ambient environment (extracellular fluids) and continue to live by retaining the difference between these two environments. To this end, energy must be constantly produced and supplied to the brain cells. Most of the energy that is required by nerve cells in the brain is supplied by oxygen and glucose but the brain has a very limited reserve of these energy sources and must be constantly fed with additional supplies from the blood stream.

If a certain disorder occurs in the brain and the supply of oxygen and glucose is discontinued, cacochymia of energy generally occurs progressively and the brain cells will lose their functions with the elapse of time and will eventually collapse organically to become no longer capable of fulfilling their functions. Therefore, in order to ensure a stable supply of the necessary energy sources to the brain tissues and provide a controlled external environment for cranial nerve cells, the human cerebral vessels are equipped with a well developed mechanism for adjusting the blood stream in the brain.

Conventional non-surgical therapy for cerebrovascular disorders has involved the use of a variety of drugs for improving the cerebral circulation, dilating the blood vessels or for improving the brain metabolism. These drugs are effective in ameliorating the subjective symptoms of patients but are little effective in lessening their neurotic or psychic symptoms. In addition, no compound has previously been known that can be used as a psycho-pharmaceutical exhibiting capabilities of brain protection end improving the cerebral circulation as does the compound of the present invention.

The present inventors conducted extensive studies for many years in order to find compounds that would be effective in ameliorating and eliminating symptoms that result either from the aforementioned organic disorders in the brain or on account of pathergasia. As a result, the inventors have found that the novel oxabicycloheptane derivatives of the present invention and pharmaceutically acceptable salts thereof are very effective against the formation of peroxylipids and the deficiency of oxygen in a variety of cranial nerve cells (brain anoxia), two factors that are believed to be closely associated with organic disorders in the brain and pathergasia as described above. In addition, these derivatives and pharmaceutically acceptable salts thereof were found to have surprisingly high activities against depression and to be very useful as psychopharmaceuticals. The present invention has been accomplished on the basis of these findings.

SUMMARY OF THE INVENTION

The novel oxabicycloheptane derivative of the present invention shows the ability to improve the brain functions of a laboratory animal model under various anoxic conditions even when it is used in a low dose. The derivative also has an anti-lipidperoxidation activity and exhibits a strong anti-depression effect for a laboratory animal model subjected to forced swimming. Because of these capabilities, the compound of the present invention is useful not only in improving and treating organic disorders in the brain and pathergasis but also as a psychotherapeutic.

DETAILED DESCRIPTION OF THE INVENTION

The present invention relates to an oxabicycloheptane derivative of the following general formula (I) or a pharmaceutically acceptable salt thereof:

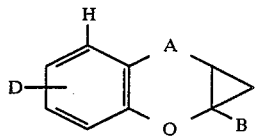
(I)

where D is a hydrogen atom, a halogen atom, a hydroxyl group, an alkoxy group, an arylalkoxy group, an acyloxy group, a dialkylcarbamoyloxy group or an amidoalkyloxy group; B is a substituted or unsubstituted phenyl, thienyl or furyl group; $\diagup A \diagdown$ is the group

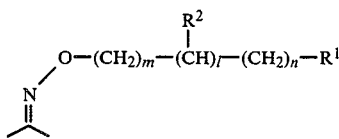

(where l is 0 or 1; m and n are each 1 or more, provided that m+n is an integer of 2-8; $R^1$ is an alkylamino group, a dialkylamino group, an arylalkylamino group, a morpholino group, a thiomorpholino group, a 1-pyrrolidinyl group, a piperidino group, an N-alkylpiperazinyl group, an N-hydroxyalkylpiperazinyl or a pyrrolizidinyl group; and $R^2$ is a lower alkyl group or a hydroxyl group), or the group

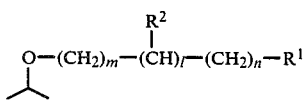

(where l, m, n, $R^1$ and $R^2$ are each the same as defined above), or the group

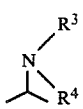

(where $R^3$ and $R^4$ which may be the same or different each represents a hydrogen atom, a lower alkyl group, an alkoxycarbonyl group or an acyl group), or the group

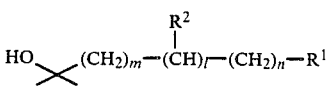

(where m, l, n, $R^1$ and $R^2$ are each the same as defined above).

The novel oxabicycloheptane derivative of formula (I) may be produced by a variety of methods. One method starts with a known compound, 3,4-benzo-5-oxo-1-phenyl-2-oxabicyclo[4.1.0]heptane (see P. Bennett et al., J. Chem. SOc., Perkin Trans. 1, (12), 2990 (1979)) or an oxabicycloheptanone derivative of formula (II) that may be synthesized by the same process as is employed in preparing said known compound:

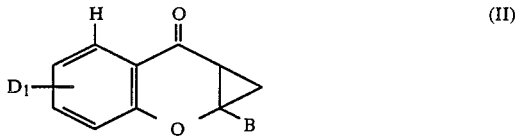
(II)

(where B is the same as defined for formula (I); $D_1$ is a hydrogen atom, a halogen atom, a lower alkoxy group or a benzyloxy group). Either compound is reacted with a hydroxylamine, a hydroxylamine hydrochloride or a hydroxylamine sulfate in the presence of a base, and the product is separated and purified by chromatography to obtain an oxime compound of the general formula (IIIa or IIIb);

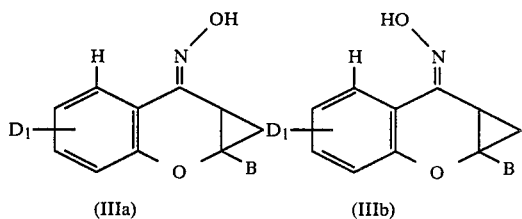

(where B and $D_1$ are each the same as defined above).

In the reaction described above, the base is preferably selected from among pyridine, sodium hydroxide, potassium hydroxide, sodium carbonate and potassium carbonate. If a solvent is used, it is preferably selected from among pyridine, water, alcohol, and a mixture of water and alcohol.

The oxime compound (IIIa or IIIb) is then reacted with a halide of the general formula (IV):

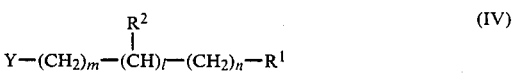
(IV)

(where m, l, n, $R^1$ and $R^2$ are each the same as defined above; and Y is a halogen atom) in the presence of a base, to thereby obtain an oxabicycloheptane derivative of the general formula (Ia or Ib):

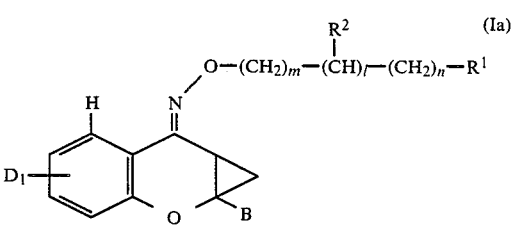
(Ia)

-continued

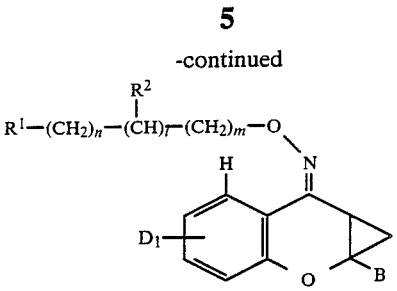
(Ib)

where B, $D_1$, m, l, n, $R^1$ and $R^2$ are each the same as defined above.

In the reaction between the oxime compound and the halide, the base used as a catalyst is preferably an alkali metal base such as lithium hydride, sodium hydride, potassium hydride, sodium amide, sodium alkoxide or potassium alkoxide, with sodium hydride being particularly suitable. If a reaction solvent is used, it is preferably selected from ether, tetrahydrofuran, dioxane, and aromatic hydrocarbons such as benzene, toluene and xylene.

The oxabicycloheptane derivative (Ia or Ib) may also be prepared by the following process. The oxime compound of the general formula (IIIa or IIIb) is reacted with a dihalide of the general formula (V):

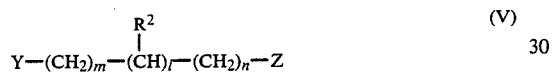
(V)

(where Y, m, l, n and $R^2$ are each the same as defined above; and Z is a halogen atom) in the presence of a base to obtain a halide of the general formula (VIa or VIb):

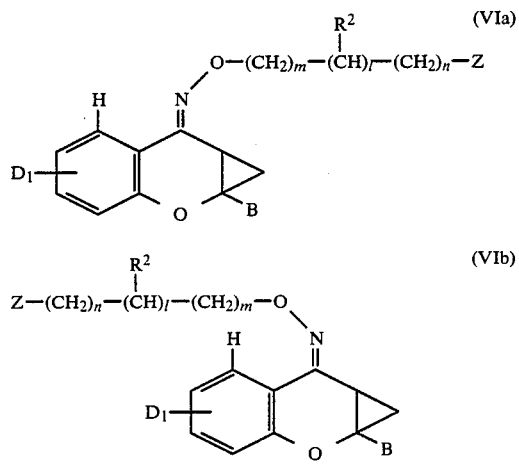
(VIa)

(VIb)

(where B, $D_1$, m, l, n, $R^2$ and Z are each the same as defined above). The resulting halide is heated together with an amine of the general formula (VII):

$R^1$—H  (VII)

(where $R^1$ is the same as defined above) in a solvent such as dioxane or tetrahydrofuran to obtain the compound of formula (Ia) or (Ib). The base and solvent used in the reaction between the oxime compound (IIIa or IIIb) and the dihalide (V) are preferably the same as those employed in direct production of the compound (Ia or Ib) by reacting the compound (IIIa or IIIb) with the halide (IV).

When the oxime compound (IIIa or IIIb) is reduced by a conventional method, an amino compound of the general formula (Ic) is obtained:

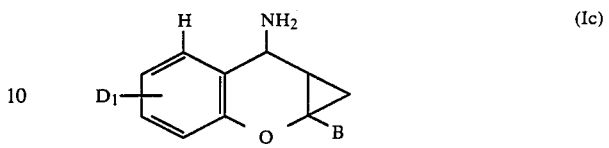
(Ic)

where B and $D_1$ are each the same as defined above. In this reaction, any reagent that is capable of reducing the oxime may be used as a reducing agent and lithium aluminium hydride is particularly advantageous. Any solvent that is inert to the reaction may be used and a preferable solvent is ether, tetrahydrofuran or dioxane.

The amino compound (Ic) is then reacted with an acyl halide or acid anhydride of the general formula (VIII):

$R^5COY$ or $(R^5CO)_2$  (VIII)

($R^5$ is a lower alkyl group or a halogenoalkyl group; and Y is a halogen atom) in the presence of a base to obtain an amide compound of the general formula (Id):

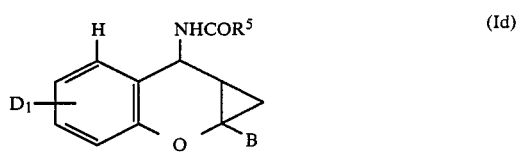
(Id)

where B, $D_1$ and $R^5$ are each the same as defined above.

In this reaction for obtaining the amide compound (Id), the base is preferably selected from pyridine, trialkylamines and alkali hydroxides. Any solvent that is inert to the reaction may be employed.

An amide compound of the formula (Id) wherein $R^5$ is a halogenoalkyl group may be reacted with 2-pyrrolidone by a conventional method so as to synthesize 2-pyrrolidonyl compounds of general formula (Id): (where B and $D_1$ are each the same as defined above the $R^5$ is 2-pyrrolidon-1-yl alkyl group).

The amide compound (Id) wherein $R^5$ is a lower alkyl group may be reduced by a conventional method to obtain an amino compound of the general formula (Ie):

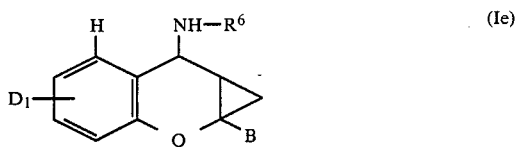
(Ie)

(where B and $D_1$ are each the same as defined above and $R^6$ is lower alkyl group). Lithium aluminum hydride is most optimum for use as a reducing agent. If a solvent is used, it is preferably selected from ether or tetrahydrofuran.

The amino compound (Ie) thus obtained may be reacted with an acyl halide or acid anhydride of the general formula (VIII): in the presence of a base, to thereby obtain an amide compound of the general formula (If):

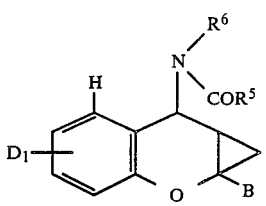

where B, $D_1$, $R^5$ and $R^6$ are each the same as defined above. The base used in this reaction is preferably selected from among pyridine, trialkylamines and alkali hydroxides. Any solvent may be used so long as it is inert to the reaction.

The amide compound (If) thus obtained may be reduced by the same method as used to reduce the compound (Id), and this provides an amine derivative of the general formula (Ig):

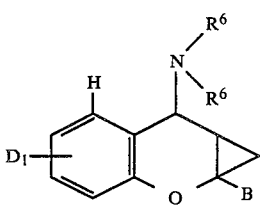

where B, $D_1$, and $R^6$ are each the same as defined above. A dialkyl compound of formula (Ig) may also be produced by reacting the amino compound (Ic) with two molecules of an alkyl halide in the presence of a base by a conventional method.

The amino compound (Ic) is also reacted with alkylchlorocarbonate by a conventional method to obtain the general formula (Ih):

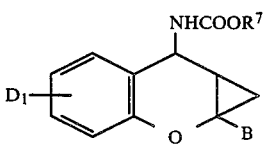

(where B and $D_1$ are the same as defined above and $R^7$ is lower alkyl group).

When the oxabicycloheptanone derivative of formula (II) is reduced by a conventional method, an alcohol of the general formula (IX) is produced:

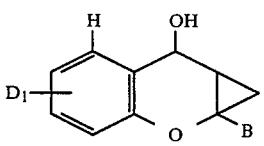

where B and $D_1$ are each the same as defined above. Any compound that is capable of reducing ketone without acting upon the fused rings in formula (II) may be used as a reducing agent and sodium borohydride is most preferably used. Any solvent that is inert to the reaction may be employed.

By reacting the alcohol (IX) with the compound (IV) in the presence of a base, an ether compound of the general formula (Ii) may be obtained:

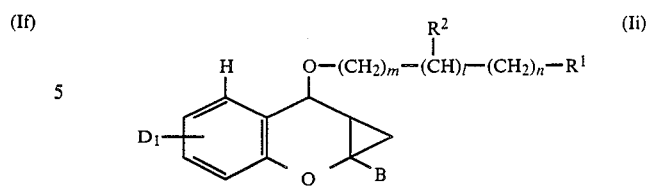

where B, $D_1$, m, l, n, $R^1$ and $R^2$ are each the same as defined above. The base and solvent that are used in this reaction are the same as those employed in synthesizing the oxabicycloheptane derivative of formula (Ia) or (Ib).

The ether compound (Ii) may also be produced by the following method. An alcohol of formula (IX) is reacted with a dihalide of formula (V) to prepare a halide of the general formula (X):

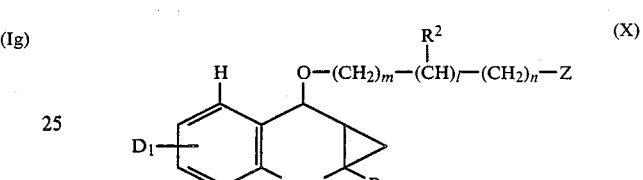

where B, $D_1$, m, l, n, $R^2$ and Z are each the same as defined above. The halide is reacted with an amine of formula (VII) to obtain a compound of the present invention that is represented by formula (Ii). Reaction by this route may be carried out using the same base and solvent as are employed in preparing the compound of formula (Ia) or (Ib) from the compound of (IIIa or IIIb) via the compound (VIa or VIb).

The oxabicycloheptanone derivative (II) may be reacted with an excess of a Grignard reagent of the general formula (XI):

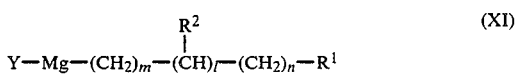

(where Y, m, l, n, $R^1$ and $R^2$ are each the same as defined above) to obtain an oxabicycloheptanol derivative of the general formula (Ij):

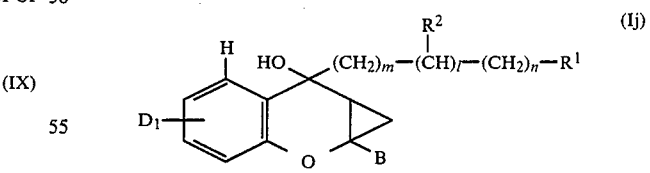

where B, $D_1$, m, l, n, $R^1$ and $R^2$ are each the same as defined above. Preferably the solvent used in this reaction is ether, tetrahydrofuran or dimethoxyethane. The amount of Grignard reagent used may be one equivalent but is preferably within the range of 1.2–1.5 equivalents.

Among the compounds of formulas (Ia) to (Ij) that are synthesized by the methods described above, a compound of the following general formula wherein $D_1$ is a benzyloxy group:

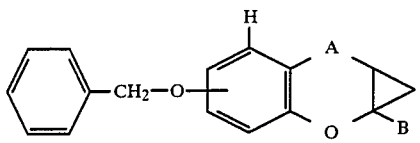

(where A and B are each the same as defined above) may be reduced by a conventional method to obtain a phenol derivative of the general formula (Ik):

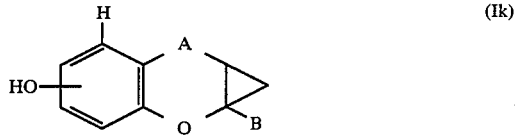

where A and B are each the same as defined above. Any conventional catalyst may be used in this reaction and palladium-on-carbon is most preferably used. Any solvent may be employed so long as it is inert to the reaction.

The phenol derivative of formula (Ik) may be reacted with a halide or an acid anhydride to obtain a compound of the following general formula (II) having an acyloxy, dialkylcarbamoyl or amidoalkyloxy group:

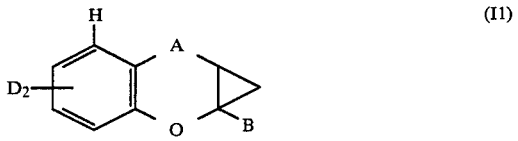

where A and B are each the same as defined above, and $D_2$ is an acyloxy, dialkylcarbamoyl or amidoalkyloxy group.

Compounds of the present invention which have an amino group in a side chain may be dissolved in an appropreate organic solvent such as ether, tetrahydrofuran, methylene chloride, chloroform, benzene or toluene and treated with an inorganic or organic acid to obtain a corresponding salt. Illustrative organic acids that can be used include formic acid, acetic acid, oxalic acid, malonic acid, propionic acid, butyric acid, valeric acid, succinic acid, fumaric acid, maleic acid, tartaric acid and benzoic acid; illustrative inorganic acids are hydrochloric acid, phosphoric acid and periodic acid.

The compounds of the present invention have not only brain-protection but also anti-lipidperoxidation, anti-amnesia, brain circulation-improving, anti-platelet aggregation and anti-depression effects. The activites of these effects were evaluated by the following methods.

1. Anti-cerebroischemic effect (i.e., brain protection after ischemia by decapitation)

Male ddY mice weighing 22–30 g were used in groups each consisting of 6 animals. Test compounds were administered intraperitoneally to the mice which were decapitated 30 minutes after the administration. The gasping time, or the duration of time between the onset of panting after decapitation and its cessation, was measured, and this was compared with the gasping time for a control group which were given only a liquid vehicle.

Results

Only the compounds prepared in Examples 1, 2, 7, 8, 9, 20, 21, 23, 24, 26, 27, 28 and 30 were capable of significantly prolonging the gasping time in an amount of 25 mg/kg. Among these compounds, those prepared in Examples 2, 21, 23, 24, 27 and 28 achieved significant prolongation of the gasping time in an amount of 12.5 mg/kg.

2. Anti-hypoxia effect (i.e., grain protection in low-oxygen state after evacuation)

Male ddY m8mice weighing 22-30 g were used in groups each consisting of 7-10 animals. The mice were placed in a desiccator (capacity: ca. 1,000 ml) which was evacuated with a vacuum pump to an internal pressure of 180 mmHg after intraperitoneal administration of test compounds. The survival time, or the duration of time between the start of evacuation and the cessation of breathing, was measured, and this was compared with the value for a vehicle group. Any survival time longer than a period of 15 minutes after application of a hypoxia load was counted as 15 minutes.

Results

Only the compounds prepared in Examples 2, 4, 5, 11, 15, 21, 30 and 31 were capable of significantly prolonging the survival time in an amount of 12.5 mg/kg. Among these compounds, those prepared in Examples 2, 30 and 31 achieved significant prolongation of the survival time in amounts of 6.25 mg/kg or smaller.

3. Anti-lipidperoxidation effect

Male Wistar rats weighing 200–250 g were used. The brain of each rat was extracted after decapitation, homogenized with 50 mM of a phosphate buffer solution (PBS, pH 7.4) and centrifuged at 1,000 g for 15 minutes. The supernatant was stored frozen at $-30°$ C. Before use, it was thawed under flowing water and diluted with PBS three-fold to prepare a live sample.

Two samples were prepared by adding 10 $\mu$l ($10^{-4}$M) of a test compound in solution to 990 $\mu$l of the live sample. One sample was incubated at 37° C. for 30 minutes and reaction was quenched by addition of 0.2 ml of 35% aqueous perchloric acid. The other sample was immediately mixed with 35% perchloric acid without incubation. Each of the mixtures was centrifuged at 3,000 rpm for 15 minutes and 0.5 ml of the supernatant was subjected to TBA assay (Yagi et al., Anal. Biochem., 95, 351 (1979)) for determining the malondialdehyde (MDA) content ($\times 10^{-4}$M) by subtracting the peroxylipid level for the unincubated mixture from that for the incubated mixture. The percent inhibition of peroxylipid formation was calculated by the following formula:

$$\text{Percent inhibition of peroxylipid formation} = \frac{B - A}{B} \times 100 \ (\%)$$

where A is the MDA content of a treated sample and B is the value for a control sample that was not treated with any test compound.

Results

The test results are shown in Table 1 from which one can see that strong anti-lipidperoxidation effects were exhibited by the compounds prepared in Examples 5, 8, 9, 12, 15 and 16.

TABLE 1

| Example No. | Inhibition of peroxylipid formation (%) | Example No. | Inhibition of peroxylipid formation (%) |
| --- | --- | --- | --- |
| 1 | 56.9 | 19 | 52.6 |
| 4 | 56.0 | 21 | 62.1 |
| 5 | 96.5 | 26 | 79.1 |
| 8 | 90.2 | 27 | 62.0 |

TABLE 1-continued

| Example No. | Inhibition of peroxylipid formation (%) | Example No. | Inhibition of peroxylipid formation (%) |
|---|---|---|---|
| 9 | 82.7 | 28 | 77.6 |
| 12 | 99.0 | 34 | 79.9 |
| 15 | 85.7 | 35 | 69.0 |
| 16 | 83.3 | | |

4. Effect on blood flow in the vertebral artery, blood pressure and heart rate in anesthetized dogs Mongrel dogs of either sex, weighing 6.8–9.4 kg, were used. The animals were anesthetized with an intravenous injection, at first, of 30 mg/kg of sodium thiopental and thereafter, of a combination of urethane 400 mg/kg and α-chloralose 60 mg/kg. Under artificial ventilation (20 ml/kg/stroke, 20 strokes/min), blood flow in the vertebral artery and blood pressure were measured with the aid of an extracorporeal electromagnetic flow probe placed on the artery and a pressure transducer, respectively. Vertebral vascular resistance was recorded with an electronic divider and heart rate was measured with a heart rate counter triggered by blood pressure pulses. All of these parameters were recorded on a polygraph continuously. When these parameters became stable, test compounds were injected into the femoral vein.

Results and discussion

At doses of 0.3 and 1.0 mg/kg, compound No. 2 produced dose-dependent decreases in vertebral vascular resistance but almost no change in blood pressure and heart rate. At a dose of 3.0 mg/kg, compound No. 2 produced a further decrease in vertebral vascular resistance concomitant with a small decrease in blood pressure, and an increase in heart rate.

5. Effect on in vitro platelet aggregation

Arterial blood was drawn from the ear artery of male Japanese white rabbits. Platelet rich plasma (PRP) was prepared by centrifugation of 9 ml of blood mixed with 1 ml of 3.8% sodium citrate as anticoagulant. Platelet aggregation was measured optically according to Born's method. ADP (10 μM), collagen (37.5 μg/ml), platelet activating factor (PAF, 0.11 nM) and calcium ionophore A 23187 (1 μg/ml) were used as platelet aggregators. Test compounds were added 1 minute prior to the addition of aggregating agents.

Results and discussion

Compound No. 2 caused decreases in platelet aggregation induced by all the aggregators used. $IC_{50}$ (50% inhibitory concentration) obtained were shown in Table 2.

These results suggest that, like calmodulin antagonists (W-7 and chlorpromazine), compound No. 2 has nonspecific inhibitory actions on in vitro platelet aggregation.

TABLE 2

| | Effects on platelet aggregation in rabbit platelet rich plasma | | | | |
|---|---|---|---|---|---|
| | Anti-platelet aggregation $IC_{50}$ (μg/ml) | | | | |
| | ADP | Collagen | AA | PAF | A 23187 |
| Compound No. 2 | 34.5 | 4.1 | 54.0 | 20 | 69 |
| Calmodulin antagonist W-7 | 18 | 11 | 11 | 27 | 19 |
| Chlorpromazine | 57 | 22 | 105 | 93 | 125 |

6a. Anti-amnesia effect (i.e., capability of preventing scopolamine-induced retrograde amnesia)

Five-week old male ddY weighing 25–30 g were used in groups each consisting of 10 animals. Memory retention deficit induced by scopolamine was evaluated by two-compartment step-through passive avoidance task. The apparatus used consisted of a light and a dark compartment separated by a partition that had a hole providing a free passage for a mouse. The floor of the dark compartment was provided with a current-conducting grid.

The experimental method was as follows. A scopolamine amnesia mouse that had been given subcutaneous injection of 0.5 mg/kg of an aqueous solution of scopolamine borate 20 minutes before was placed in the light compartment and when its forefeet touched the grid floor of the dark compartment, a current of 0.6 mA was applied to give a foot shock to the mouse (acquired conation). Immediately thereafter, a selected test compound or a control (physiological saline solution) was administered intraperitoneally. Twenty-four hours later, the mouse was replaced in the light compartment and the step-through latency, or the time required for the mouse to move to the dark compartment, was measured for a period of up to 300 seconds (test conation). The minimum effective amount of the test compound that provided a significant prolongation of the step-through latency over the control was determined.

Results

The test results are shown in Table 3.

TABLE 3

| Example No. | Minimum effective amount (mg/kg) |
|---|---|
| 2 | 3.2 |
| 7 | 20 |
| 21 | 25 |
| 23 | 50 |
| 28 | 12.5 |
| 30 | 12.5 |

6b. Effects on electroconvulsive shock (ECS)- and cycloheximide-induced amnesia in mice Male, ddY strain mice, weighing 25 to 35 g, were used. Memory retention deficit induced by ECS and cycloheximide was evaluated by two-compartment step-through passive avoidance task using a light-dark apparatus. Passive avoidance training test began by placing the mouse into the light compartment. When the mouse moved completely into the dark compartment, a shock of 0.6 mA was applied from the grid floor. Amnesia was induced in the following two ways. In the first one, a single ECS (current 50 mA, frequency 50 Hz, pulse width 1 msec, shock duration 1 msec) was applied via a pair of electrodes attached to the head immediately after receiving the foot shock, and the mouse was returned to its home cage. Test compounds were administered intraperitoneally 30 minutes before a retention test. In the second one, cycloheximide (40 mg/kg) was administered subcutaneously 30 minutes before the training and the compounds in question were administered intraperitoneally immediately after the training. A retention test was given 24 hours later. The test procedures proceeded in a manner similar to the training one, and time to entry into the dark compartment was measured for 300 seconds.

Results

Intraperitoneal administrations of compound No. 2 significantly prevented the ECS-induced shortening of step-through latency at doses of 6.25 and 12.5 mg/kg.

Furthermore, this compound also significantly prolonged the step-through latency to be shortened by cycloheximide treatment, when given intraperitoneally at doses of 6.25 and 50 mg/kg.

7. Anti-depression effect

Male ICR mice weighing 25–30 g were used in groups each consisting of 6 or 7 animals. In accordance with the method of Nomura et al. (S. Nomura et al., Europ. J. Pharmacol., 83, 171 (1982)), the anti-depression effect was evaluated in terms of the number of revolutions of a water wheel in a water container in which a mouse was placed and forced to swim for 15 minutes. First, the mouse was subjected to force swimming for two days on a 15-minutes-a-day basis; starting on the third day, the mouse that had received intraperitoneal injection of a test compound one hour before was subjected to forced swimming for 3 days on a 15-minutes-a-day basis. The compound prepared in Example 2 was found to have an anti-depression effect because the mouse injected with 50 mg/kg of this compound rotated the water wheel 1.8 times as fast as the control group.

EXAMPLES

This invention is particularly illustrated by the following examples but the technical scope of this invention is not to be limited by them.

REFERENCE EXAMPLE 1

3,4-Benzo-5-hydroxyimino-1-phenyl-2-oxabicyclo[4.1.0]heptane (IIIc, IIId)

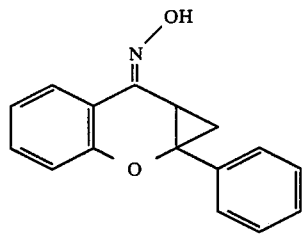

(IIIc)

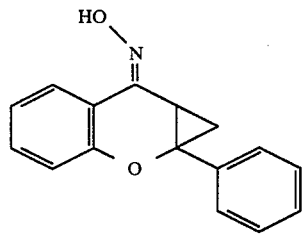

(IIId)

2.4 g of 3,4-benzo-5-oxo-1-phenyl-2-oxabicyclo[4.1.0]heptane was dissolved in 80 ml of pyridine and 2.83 g (four equivalents) of hydroxyl amine hydrochloride was added to the solution. The mixture was stirred at 55° C. for 2 hours. The reaction was concentrated, diluted with water and extracted with chloroform. The extracts were washed with water, dried over anhydrous magnesium sulfate, filtered and concentrated.

The residue was purified by chromatography on silica gel (hexane:ethyl acetate 9:1) to produce the titled compounds (IIIc, 2.35 g, 92.1%) and (IIId, 0.159 g, 6.23%).

REFERENCE EXAMPLES 2–6

In a manner similar to Reference Example 1, the following compounds were obtained in Reference Examples 2–6.

REFERENCE EXAMPLE 2

3,4-(3-Methoxybenzo)-5-hydroxyimino-1-phenyl-2-oxabicyclo[4.1.0]heptane

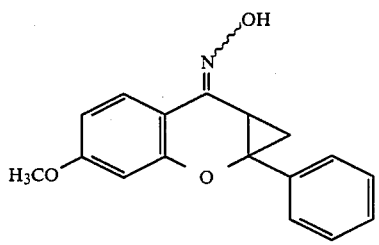

Yield: 90%

REFERENCE EXAMPLE 3

3,4-(3-Chlorobenzo)-5-hydroxyimino-1-phenyl-2-oxabicyclo[4.1.0]heptane

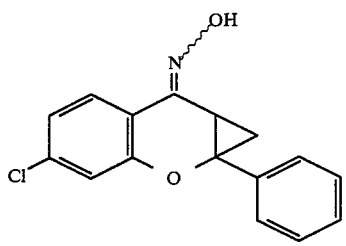

Yield: 95.3% m.p.: 157.5°–159° C.

REFERENCE EXAMPLE 4

3,4-(3-Benzyloxybenzo)-5-hydroxyimino-1-phenyl-2-oxabicyclo[4.1.0]heptane

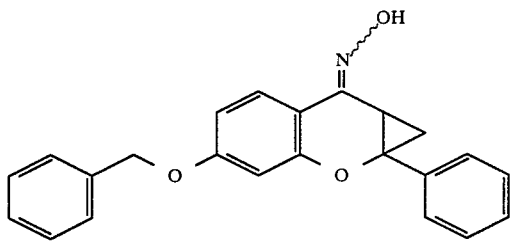

Yield: 92.4%

REFERENCE EXAMPLE 5

3,4-Benzo-5-hydroxyimino-1-thienyl-2-oxabicyclo[4.1.0]heptane

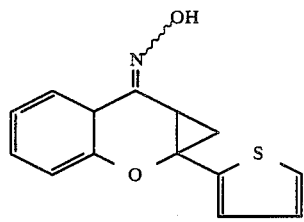

Yield: 86%

REFERENCE EXAMPLE 6

3,4-(3-Chlorobenzo)-5-hydroxyimino-1-(4-nitrophenyl)-2-oxabicyclo[4.1.0]heptane

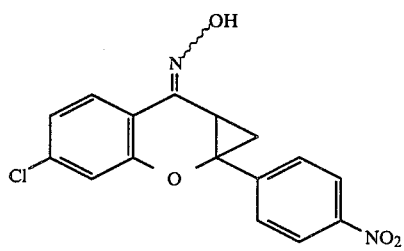

Yield: 74.4%
m.p.: 176°–177° C.

REFERENCE EXAMPLE 7

3,4-Benzo-5-(2-bromoethyl)oxyimino-1-phenyl-2-oxabicyclo[4.1.0]heptane

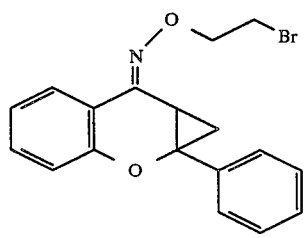

700 mg of the product (IIIc) obtained in Reference Example 1 was dissolved in 60 ml of tetrahydrofuran and 223 mg (2 equivalent) of sodium hydride as a 60% oil was added. The mixture was refluxed for one hour and 3.14 g (6 equivalents) of ethylenedibromide was added. The mixture was refluxed for 5 hours. After evaporating the solvent, ice-water was added. The reaction was extracted with ether and the ether layer was washed with water, dried over anhydrous magnesium suflate, filtered and concentrated and the residue was subjected to chromatography on silica gel (hexane:ethyl acetate 95:5) to produce 911 mg (yield 91.3%) of the titled compound.

REFERENCE EXAMPLES 8–10

The products in Reference Examples 8–10 were synthesized in a manner similar to Reference Example 7.

REFERENCE EXAMPLE 8

3,4-Benzo-5-(3-chloropropyl)oxyimino-1-phenyl-2-oxabicyclo[4.1.0]heptane

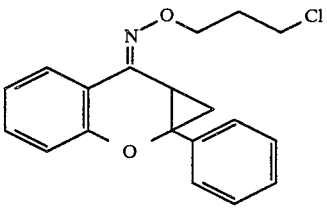

Yield: 88.3%

REFERENCE EXAMPLE 9

3,4-Benzo-5-(4-bromobutyl)oxyimino-1-phenyl-2-oxabicyclo[4.1.0]heptane

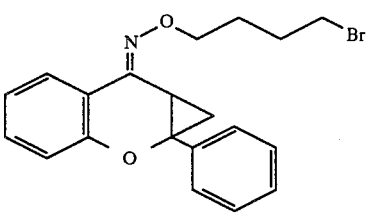

Yield: 100%

REFERENCE EXAMPLE 10

3,4-Benzo-5-(5-bromopentyl)oxyimino-1-phenyl-2-oxabicyclo[4.1.0]heptane

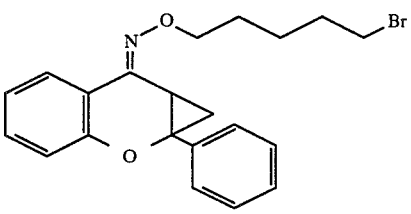

Yield: 81.0%

REFERENCE EXAMPLE 11

3,4-Benzo-5-hydroxy-1-phenyl-2-oxabicyclo[4.1.0]heptane

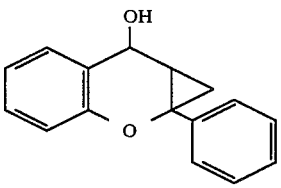

1.14 g of 3,4-benzo-5-oxo-1-phenyl-2-oxabicyclo[4.1.0]heptane was dissolved in 60 ml of methanol and sodium borohydride was added to the solution under cooling in ice. The mixture was stirred at room temperature for 2 hours. After evaporating the solvent, ice water was added to the residue and the mixture was extracted with ether. The ether layer was washed with water, dried over anhydrous magnesium sulfate, filtered and concentrated and the residue was purified by column chromatography on silica gel (hexane:ethyl acetate 9:1) to obtain 1.07 g of the titled compound (93.1%) as a mixture of stereoisomers.

REFERENCE EXAMPLES 12-14

The products in Reference Examples 12-14 were prepared in a manner similar to Reference Example 11.

REFERENCE EXAMPLE 12

3,4-(3-Chlorobenzo)-5-oxo-1-phenyl-2-oxabicyclo[4.1.0]heptane

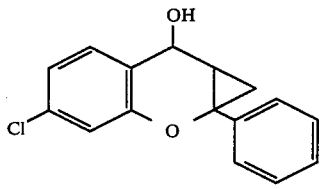

Yield: 95.3%

REFERENCE EXAMPLE 13

3,4-(3-Methoxybenzo)-5-hydroxy-1-phenyl-2-oxabicyclo[4.1.0]heptane

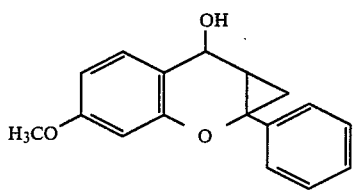

Yield: 93.3%

REFERENCE EXAMPLE 14

3,4-(3-Benzyloxybenzo)-5-hydroxy-1-phenyl-2-oxabicyclo[4.1.0]heptane

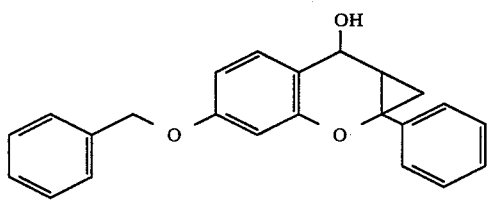

Yield: 96.7%

REFERENCE EXAMPLE 15

3,4-Benzo-5-(4-bromobutyl)oxy-1-phenyl-2-oxabicyclo[4.1.0]heptane

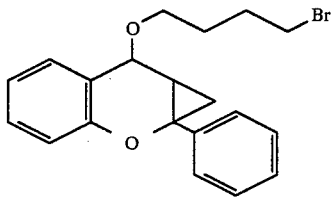

3.14 g of the product obtained in Reference Example 11 was reacted with 6.49 ml of 1,4-dibromobutane in the presence of 1.07 g of sodium hydride in a manner similar to Reference Example 7 and the product was purified to obtain 3.07 g of the title compound (72.7 g).

REFERENCE EXAMPLES 16-17

The products obtained in Reference Examples 16 and 17 were prepared in a manner similar to Reference Example 15.

REFERENCE EXAMPLE 16

3,4-Benzo-5-(6-bromohexyl)oxy-1-phenyl-2-oxabicyclo]4.1.0]heptane

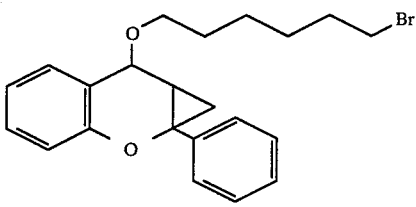

Yield: 72.4%

REFERENCE EXAMPLE 17

3,4-(3-Benzyloxybenzyl)-5-(4-bromobutyl)oxy-1-phenyl-2-oxabicyclo[4.1.0]heptane

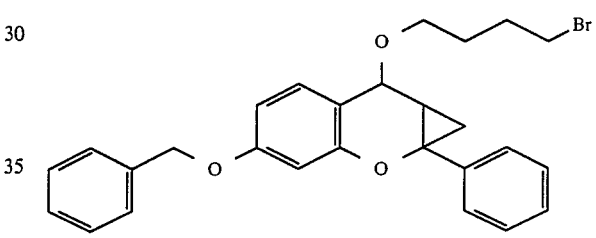

The product obtained in Reference Example 14 was used to produce the title compound in a yield of 54%.

WORKING EXAMPLE 1

3,4-Benzo-5-(2-dimethylaminoethyl)oxyimino-1-phenyl-2-oxabicyclo[4.1.0]heptane

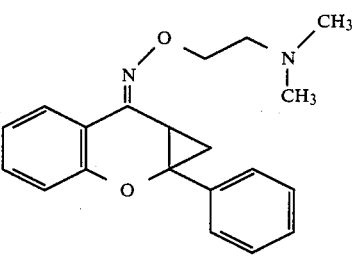

600 mg (2.39 mmol) of compound IIIc obtained in Reference Example 1 was dissolved in 20 ml of tetrahydrofuran. 382 mg (9.56 mmol, 4 equivalents) of sodium hydride (as a 60% oil) and 1.54 g (7.17 mmol, 6 equivalents) of 2-dimethylaminoethyl chloride were added and the mixture was heated to reflux overnight. The reaction was concentrated and ice-water was added to the residue. The mixture was extracted with ether and the ether phase was washed with water and dried over anhydrous magnesium sulfate. After filtration, the filtrate was concentrated and the residue was subjected to chromatography on silica gel (methylene chloride:methanol 95:5) to produce 220 mg (yield 30.2%) of the titled compound as an oil.

WORKING EXAMPLES 2-12

The product obtained in Working Examples 2-12 were prepared in a manner similar to Working Example 1.

WORKING EXAMPLE 2

3,4-Benzo-5-(3-dimethylaminopropyl)oxyimino-1-phenyl-2-oxabicyclo[4.1.0]heptane

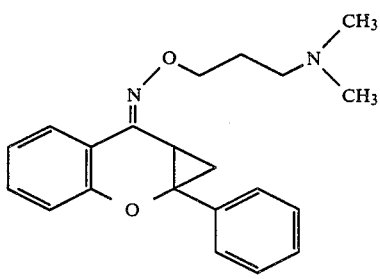

Yield: 90.7%
m.p.: 52.0°-53.0° C.

WORKING EXAMPLE 3

3,4-Benzo-5-(3-dimethylaminopropyl)oxyimino-1-phenyl-2-oxabicyclo[4.1.0]heptane

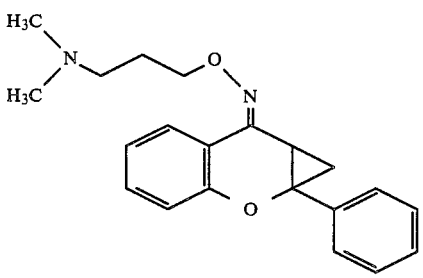

The compound (IIId) obtained in Reference Example 1 was used to produce the titled compound in a yield of 47%.

WORKING EXAMPLE 4

3,4-Benzo-5-(3-dimethylamino-2-methylpropyl)-oxyimino-1-phenyl-2-oxabicyclo[4.1.0]heptane

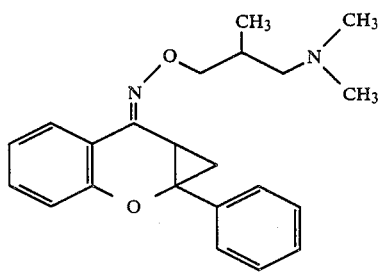

Yield: 98%

WORKING EXAMPLE 5

3,4-Benzo-5-(2-pyrrolizidin-8-ylethyl)oxyimino-1-phenyl-2-oxabicyclo[4.1.0]heptane

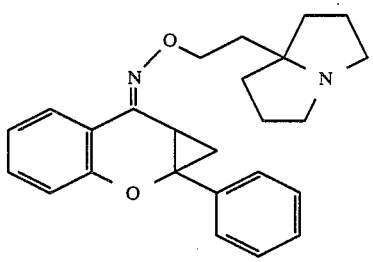

Yield: 77.5%

WORKING EXAMPLE 6

3,4-Benzo-5-[2-(4-methylpiperadinyl)-2-oxoethyl]oxyimino-1-phenyl-2-oxabicyclo[4.1.0]heptane

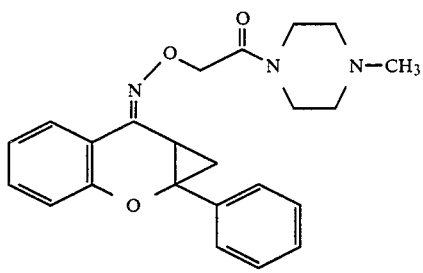

Yield: 42.3%

WORKING EXAMPLE 7

3,4-(3-Methoxybenzo)-5-(2-dimethylaminoethyl)oxyimino-1-phenyl-2-oxabicyclo[4.1.0]heptane

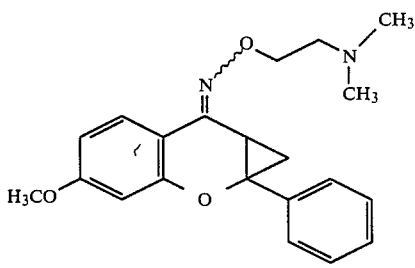

The product obtained in Reference Example 2 was used to obtain the titled compound in a yield of 71%.

WORKING EXAMPLE 8

3,4-(3-Chlorobenzo)-5-(2-dimethylaminoethyl)ox-aimino-1-phenyl-2-oxabicyclo[4.1.0]heptane

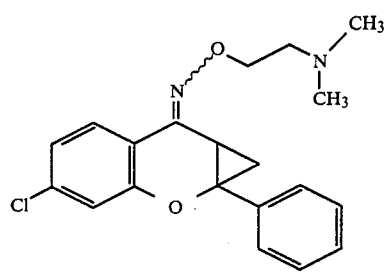

The product obtained in Reference Example 3 was used to produce the titled compound in a yield of 65.8%.

WORKING EXAMPLE 9

3,4-(3-Chlorobenzo)-5-(2-dimethylaminopropyl)ox-yimino-1-phenyl-2-oxabicyclo[4.1.0]heptane

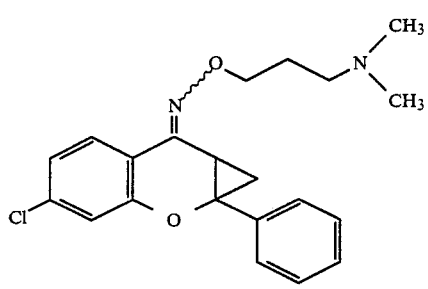

The product obtained in Reference Example 3 was used to produce the titled compound in a yield of 73.1%.

WORKING EXAMPLE 10

3,4-(3-Benzyloxybenzo)-5-(3-dimethylaminopropyl)ox-yimino-1-phenyl-2-oxabicyclo[4.1.0]heptane

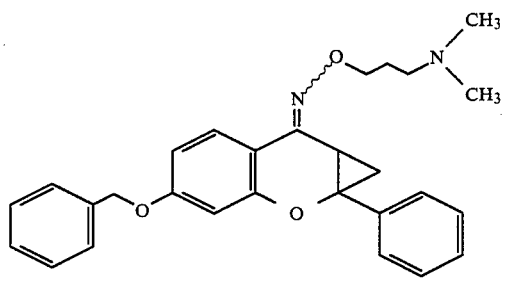

The product obtained in Reference Example 4 was used to produce the titled compound in a yield of 90.3%.

WORKING EXAMPLE 11

3,4-Benzo-5-(3-dimethylaminopropylo)xyimino-1-thienyl-2-oxabicyclo[4.1.0]heptane

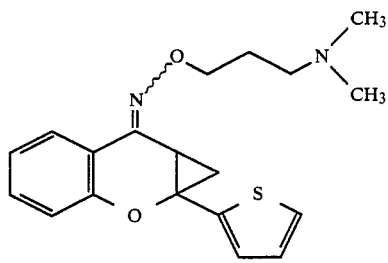

The product obtained in Reference Example 5 was used to produce the titled compound in a yield of 99.0%.

WORKING EXAMPLE 12

3,4-(3-Chlorobenzo)-5-(3-dimethylaminopropyl)ox-yimino-1-(4-nitrophenyl)-2-oxabicyclo[4.1.0]heptane

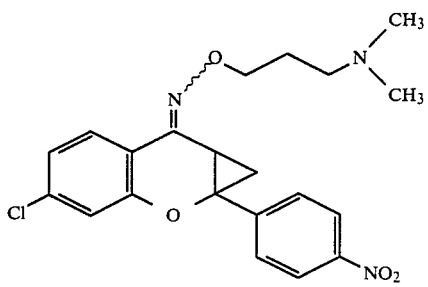

The product obtained in Reference Example 6 was used to produce the titled compound in a yield of 38.7%.

WORKING EXAMPLE 13

3,4-Benzo-5-(2-dimethylaminoethyl)oxyimino-1-phenyl-2-oxabicyclo]4.1.0]heptane

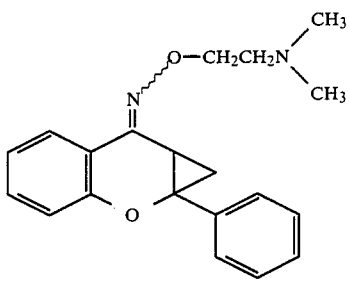

7.2 ml of 3.7M dimethylamine-tetrahydrofuran solution (20 equivalents) was added to a solution (30 ml) of 470 mg of the compound obtained in Reference Example 7 in tetrahydrofuran and the resulting mixture was heated to reflux for 10 hours. The separated crystals were filtered and the filtrate was concentrated. After adding water to the residue, the mixture was made alkaline by using ammonia and was extracted with methylene chloride. After washing the extract with water, it was dried over anhydrous magnesium sulfate. The extract was filtered and subjected to chromatography on neutral silica gel (methylene chloride:methanol 97:3) to produce 325 mg (yield 76.9%) of the same titled compound as that of Working Example 1.

WORKING EXAMPLES 14–21

The products in Working Examples 14–21 were prepared in a manner similar to Working Example 13.

WORKING EXAMPLE 14

3,4-Benzo-5-(2-morpholinoethyl)oxyimino-1-phenyl-2-oxabicyclo[4.1.0]heptane

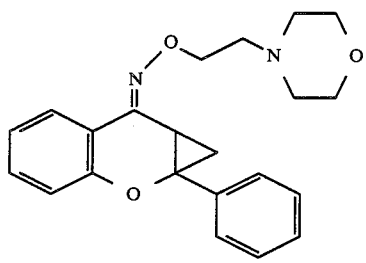

Yield: 100%

WORKING EXAMPLE 15

3,4-Benzo-5-(3-methylaminopropyl)oxyimino-1-phenyl-2-oxabicyclo[4.1.0]heptane

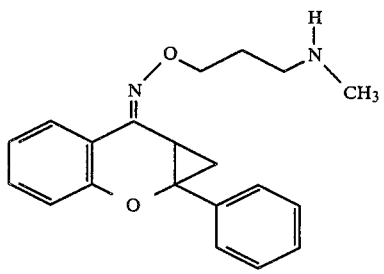

A reaction with the compound obtained in Reference Example 8 was conducted at 105° C. in a sealed tube to produce the titled compound (yield 52.3%).

WORKING EXAMPLE 16

3,4-Benzo-5-(3-dimethylaminopropyl)oxyimino-1-phenyl-2-oxabicyclo[4.3.0]heptane

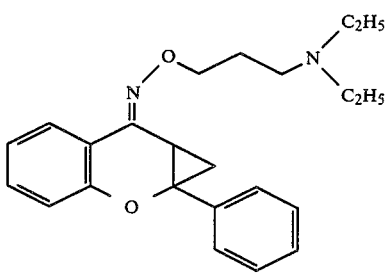

A reaction with the compound obtained in Reference Example 8 was conducted at 105° C. in a sealed tube to produce the titled compound (yield 54.8%).

WORKING EXAMPLE 17

3,4-Benzo-5-(3-pyrrolidin-1-ylpropyl)oxyimino-1-phenyl-2-oxabicyclo[4.1.0]heptane

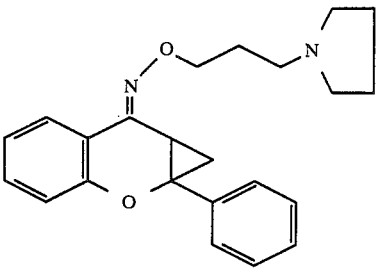

The product obtained in Reference Example 8 was used to produce the titled compound in a yield of 73.2%.

WORKING EXAMPLE 18

3,4-Benzo-5-(3-N-benzyl-N-methylaminopropyl)oxyimino-1-phenyl-2-oxabicyclo[4.1.0]heptane

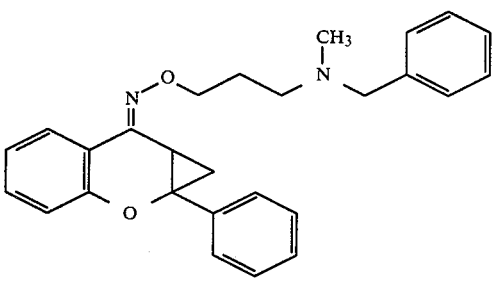

The product obtained in Reference Example 8 was used to produce the titled compound in a yield of 83.0%.

WORKING EXAMPLE 19

3,4-Benzo-5-(4-dimethylaminobutyl)oxyimino-1-phenyl-2-oxabicyclo[4.1.0]heptane

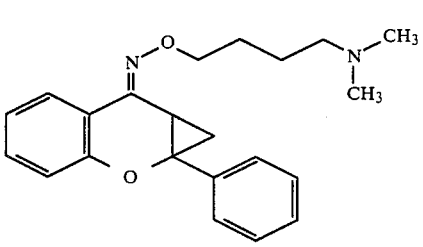

The compound obtained in Reference Example 9 was used to produce the titled compound in a yield of 87.5%.

WORKING EXAMPLE 20

3,4-Benzo-5-(4-methylaminobutyl)oxyimino-1-phenyl-2-oxabicyclo[4.1.0]heptane

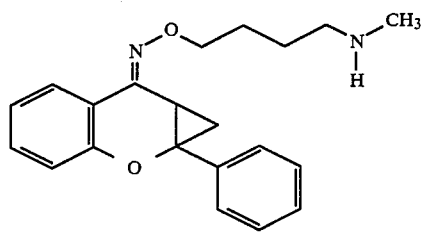

The compound obtained in Reference Example 9 was used to prepare the titled compound in a yield of 54%.

WORKING EXAMPLE 21

3,4-Benzo-5-(5-dimethylaminopentyl)oxyimino-1-phenyl-2-oxabicyclo[4.1.0]heptane

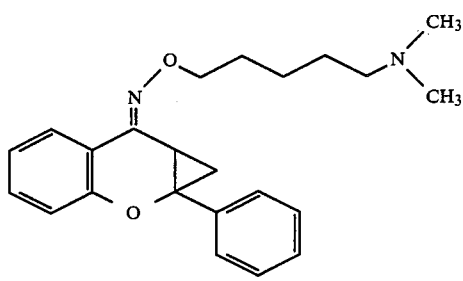

The compound obtained in Reference Example 10 was used to produce the titled compound in a quantitative yield.

WORKING EXAMPLE 22

3,4-Benzo-5-(3-pyrrolidon-1-ylpropyl)oxyimino-1-phenyl-2-oxabicyclo[4.1.0]heptane

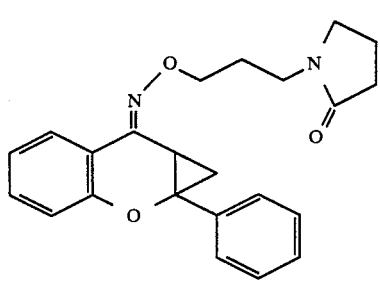

182 mg (2.4 equivalents) of sodium hydride (as a 60% oil) was added to a mixture of 194 mg of dioxane of α-pyrrolidone (10 ml) and dimethylsulfoxide (10 ml) and the mixture was heated at 110° C. for 30 minutes. A solution of 622 mg of the compound obtained in Reference Example 8 in 20 ml of dioxane was added and the mixture was heated at 110° C. for 3 hours with stirring. The reaction was concentrated and water was added. The reaction was extracted with ether. The ether layer was washed with water, dried over magnesium sulfate, filtered and concentrated. The residue was purified by chromatography on neutral silica gel (methylene chloride:methanol 98:2) to produce 326 mg (yield 46%) of the titled compound.

WORKING EXAMPLE 23

3,4-Benzo-5-(2-dimethylaminoethyl)oxy-1-phenyl-2-oxabicyclo[4.1.0]heptane

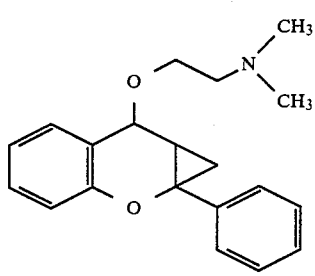

594 mg of the compound obtained in Reference Example 11 was dissolved in 50 ml of tetrahydrofuran and 200 mg (2 equivalents) of sodium hydride (as a 60% oil) was added. The mixture was heated to reflux for 30 minutes and 1.07 g (4 equivalents) of N,N-dimethylaminoethyl chloride was added. The reaction was heated to reflux for 5 hours and concentrated. Ice-water was added and the mixture was extracted with methylene chloride and the extract was washed with water, dried over anhydrous magnesium sulfate, filtrated and concentrated. The residue was purified by column chromatography on silica gel (methylene chloride:methanol 95:5) to produce 593 mg (yield 77%) of the titled compound.

WORKING EXAMPLES 24–29

The products obtained in Working Examples 14–29 were prepared in a manner similar to Working Example 23.

WORKING EXAMPLE 24

3,4-Benzo-5-(3-dimethylaminopropyl)oxy-1-phenyl-2-oxabicyclo[4.1.0]heptane

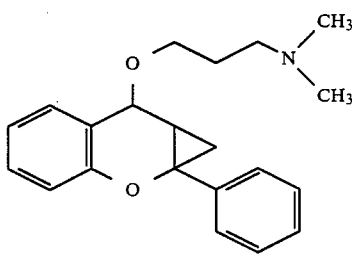

Yield: 93%

WORKING EXAMPLE 25

3,4-Benzo-5-[2-(4-methylpiperazinyl)-2-oxoethyl]oxy-1-phenyl-2-oxabicyclo[4.1.0]heptane

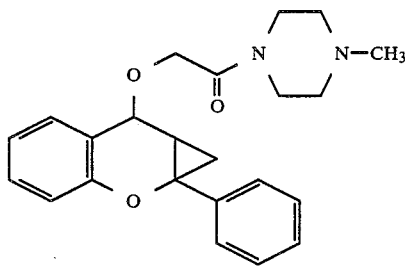

Yield: 66%

WORKING EXAMPLE 26

3,4-(3-Chlorobenzo)-5-(2-dimethylaminoethyl)oxy-1-phenyl-2-oxabicyclo[4.1.0]heptane

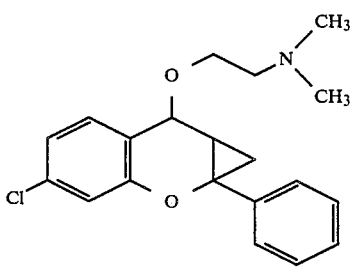

The compound obtained in Reference Example 12 was used to prepare the titled compound in a yield of 42%.

WORKING EXAMPLE 27

3,4-(3-Chlorobenzo)-5-(3-dimethylaminopropyl)oxy-1-phenyl-2-oxabicyclo[4.1.0]heptane

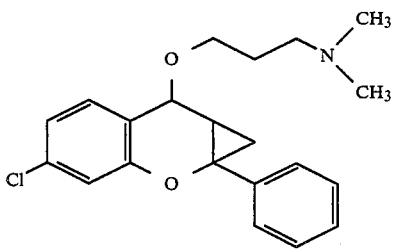

The compound obtained in Reference Example 12 was used to prepare the titled compound in a yield of 47.4%.

WORKING EXAMPLE 28

3,4-(3-Methoxybenzo)-5-(2-dimethylaminoethyl)oxy-1-phenyl-2-oxabicyclo[4.1.0]heptane

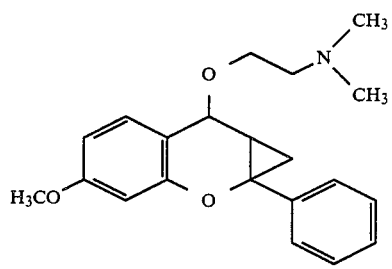

The compound obtained in Reference Example 13 was used to prepare the titled compound in a yield of 62%.

WORKING EXAMPLE 29

3,4-(3-Benzyloxybenzo)-5-(3-dimethylaminopropyl)oxy-1-phenyl-2-oxabicyclo[4.1.0]heptane

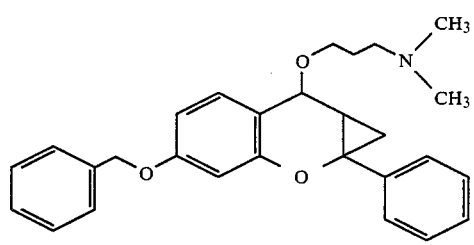

The compound obtained in Reference Example 14 was used to prepare the titled compound in a yield of 88%.

WORKING EXAMPLE 30

3,4-Benzo-5-(4-dimethylaminobutyl)oxy-1-phenyl-2-oxabicyclo[4.1.0]heptane

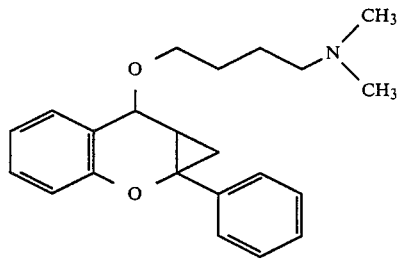

3.2 g of the compound obtained in Reference Example 15 and a large excess of dimethylamine were heated to reflux in tetrahydrofuran and treated in a manner similar to Working Example 13 to obtain 2.25 g (yield 78%) of the titled compound.

WORKING EXAMPLE 31

3,4-Benzo-5-(5-dimethylaminopentyl)oxy-1-phenyl-2-oxabicyclo[4.1.0]heptane

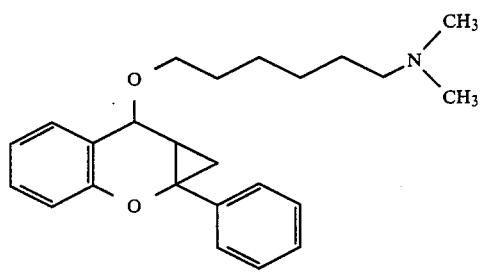

The compound obtained in Reference Example 16 was used in a manner similar to Working Example 30 to prepare the titled compound in a yield of 63.2%.

WORKING EXAMPLE 32

3,4-(3-Benzyloxybenzo)-5-(4-dimethylaminobutyl)oxy-1-phenyl-2-oxabicyclo[4.1.0]heptane

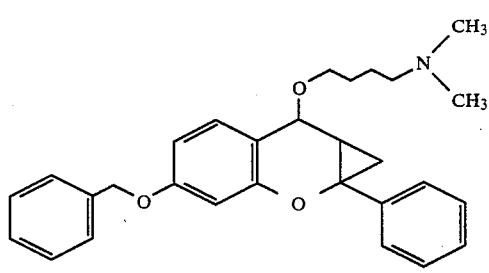

The compound obtained in Reference Example 17 was used in a manner similar to Working Example 30 to produce the titled compound in a yield of 86%.

WORKING EXAMPLE 33

3,4-Benzo-5-(4-pyrrolidon-1-ylbutyl)oxy-1-phenyl-2-oxabicyclo[4.1.0]heptane

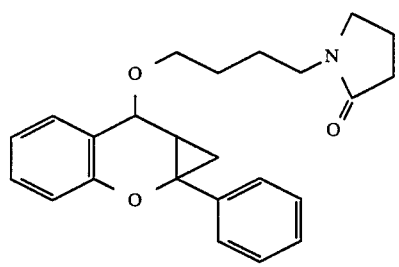

312 mg of the compound obtained in Reference Example 15, 80 mg of sodium hydride (as a 60% oil) and 85 mg of α-pyrrolidone were reacted in a mixture of 4 ml of dimethylsulfoxide and 12 ml of dioxane in a manner similar to Working Example 21 and the reaction was post-treated to obtain 1.36 mg (yield 43.3%) of the titled compound.

WORKING EXAMPLE 34

3,4-(3-Hydroxybenzo)-5-(3-dimethylaminopropyl)oxyimino-1-phenyl-2-oxabicyclo[4.1.0]heptane

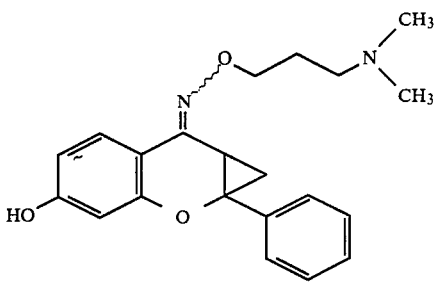

93 mg of 10% Pd-C was suspended in 6 ml of ethyl acetate and replacement with hydrogen was conducted by suction. The compound obtained in Working Example 10 was added and the mixture was stirred in an atmosphere of hydrogen (normal pressure) at room temperature for 24 hours. The reaction was filtered. The filtrate was concentrated and the residue was purified by column chromatography on silica gel (methylene chloride:methanol 90:10) to obtain the titled compound (195 mg, yield 78.7).

WORKING EXAMPLE 35

3,4-(3-Hydroxybenzo)-5-(3-dimethylaminopropyl)oxy-1-phenyl-2-oxabicyclo[4.1.0]heptane

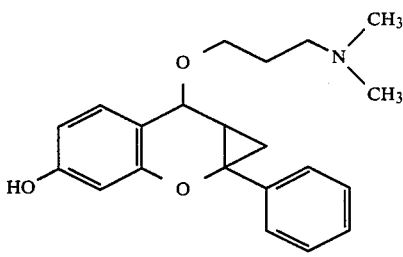

The product obtained in Working Example 29 was treated in ethanol in a manner similar to Working Example 34 to produce the titled compound in a yield of 66%.

WORKING EXAMPLE 36

3,4-(3-Hydroxybenzo)-5-(4-dimethylaminobutyl)oxy-1-phenyl-2-oxabicyclo[4.1.0]heptane

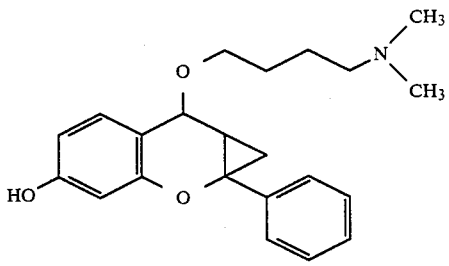

The compound obtained in Working Example 32 was treated in a manner similar to Working Example 34 to produce the titled compound in a yield of 46%.

WORKING EXAMPLE 37

3,4-(3-Acetyloxybenzo)-5-(3-dimethylaminopropyl)oxyimino-1-phenyl-2-oxabicyclo[4.1.0]heptane

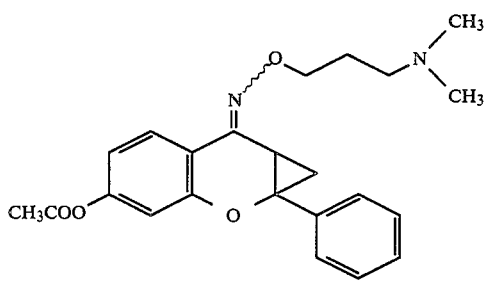

300 mg of the product obtained in Working Example 34 was dissolved in 5 ml of acetic anhydride and 10 ml of pyridine and the mixture was stirred at room temperature for one hour. The reaction was concentrated and the residue was diluted with methylene chloride and washed with a saturated aqueous solution of sodium hydrogen carbonate and then with water and dried over anhydrous magnesium sulfate. The reaction was filtered and the filtrate was concentrated. The residue was purified by column chromatography on silica gel (methylene chloride:methanol 90:10) to obtain 329 mg (yield 98%) of the titled compound.

WORKING EXAMPLE 38

3,4-(3-Acetyloxybenzo)-5-(3-dimethylaminopropyl)oxy-1-phenyl-2-oxabicyclo[4.1.0]heptane

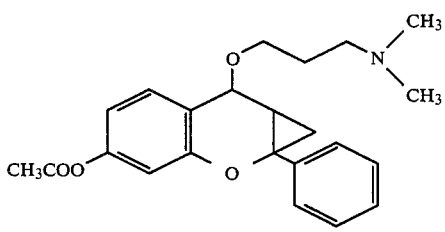

The product in Working Example 35 was treated in a manner similar to Working Example 37 to produce the titled compound in a yield of 83%.

WORKING EXAMPLE 39

3,4-(3-N,N-dimethylcarbamyloxybenzo)-5-(3-dimethylaminopropyl)oxyimino-1-phenyl-2-oxabicyclo[4.1.0]heptane

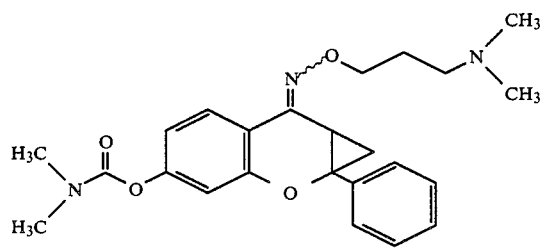

139 mg of the product obtained in Working Example 34 was dissolved in 20 ml of methylene chloride and 0.11 ml (3 equivalents) of N,N-dimethylcarbamoyl chloride and 0.55 ml (10 equivalents) of triethylamine were added to the solution. The mixture was heated to relflux for 7 hours. After cooling, the reaction was washed with an aqueous solution of sodium bicarbonate and then with water and dried over anhydrous magnesium sulfate. After filtration, the filtrate was concentrated and the residue was purified by column chromatography on silica gel (methylene chloride:methanol 95:5) to obtain 144 mg (yield 86.2%) of the titled compound.

WORKING EXAMPLE 40

3,4-[3-(2-Amino-2-oxoethyl)oxybenzo]-5-(3-dimethylaminopropyl)oxyimino-1-phenyl-2-oxabicyclo[4.1.0]heptane

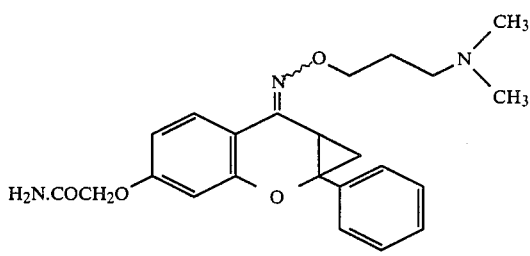

129 mg of the product obtained in Working Example 34 was dissolved in 20 ml of dioxane and 22 mg (1.5 equivalents) of sodium hydride (as a 60% oil) was added. The mixture was heated at 100° C. for 30 minutes and 72.2 mg (2 equivalents) of 2-chloroacetamide and 0.5 ml of dimethylsulfoxide were added. The mixture was stirred at 100° C. for 3 hours and the reaction was concentrated. Ice-water was added and the mixture was extracted with ether and the ether layer was washed with water and dried over anhydrous magnesium sulfate. The residue was purified by column chromatography on silica gel (methylene chloride:methanol 90:10) to obtain 94.3 mg (yield 63%) of the titled compound.

WORKING EXAMPLE 41

3,4-Benzo-5-amino-1-phenyl-2-oxabicyclo[4.1.0]heptane

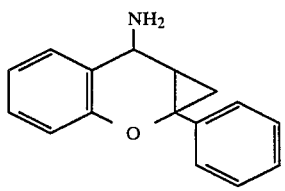

2.04 g of the product obtained in Reference Example 1 was dissolved in 100 ml of ether and 1.23 g (16 equivalents) of lithium aluminum hydride was added. The mixture was heated to reflux for 17 hours. 3N sodium hydroxide aqueous solution was added to the reaction under cooling in an ice bath to decompose excess lithium aluminum hydride.

The supernatant was separated, washed with water and dried over anhydrous magnesium sulfate. After filtration, the filtrate was concentrated and the residue was purified by column chromatography on silica gel (methylene chloride:methanol 95:5) to obtain 1.1 g (yield 57%) of the titled compound.

WORKING EXAMPLE 42

3,4-Benzo-5-ethyloxycarbonylamino-1-phenyl-2-oxabicyclo[4.1.0]heptane

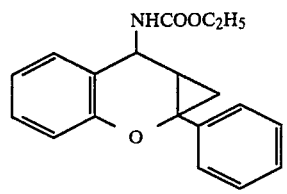

500 mg of the product obtained in Working Example 41 was dissolved in 30 ml of methylene chloride and 0.59 ml (2 equivalents) of triethyl amine and 0.3 ml (1.5 equivalents) of ethyl chlorocarbonate were added. The mixture was stirred under chilling in ice water for 30 minutes. The reaction was washed with water and dried over anhydrous magnesium sulfate. After filtration and concentration, the residue was purified by column chromatography on silica gel (hexane:ethyl acetate 85:15) to obtain 500 mg (yield 76.7%) of the titled compound.

WORKING EXAMPLE 43

3,4-Benzo-5-dimethylamino-1-phenyl-2-oxabicyclo[4.1.0]heptane

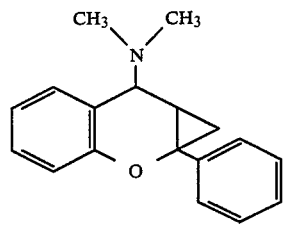

550 mg of the product obtained in Working Example 42 was dissolved in 50 ml of tetrahydrofuran and 100 mg (1.4 equivalents) of sodium hydride (as a 60% oil) was added and the mixture was heated to reflux for 30 minutes. After cooling the reaction to room temperature, 0.136 ml (1.2 equivalents) of methyl iodide was added and the mixture was stirred at room temperature for 6 hours. The reaction was concentrated and ice-water was added. The mixture was extracted with ether and the ether layer was washed with water and dried over anhydrous magnesium sulfate. After filtration, the filtrate was concentrated and the residue was purified by column chromatography on silica gel (hexane:ethyl acetate 90:10) to obtain 500 mg of a N-methylated compound. This was dissolved in 50 ml of ether and 177 mg (12 equivalents) of lithium aluminum hydride was added. The mixture was heated to reflux for 2 hours and treated in a manner similar to Working Example 41 to obtain diastereomers of the titled compound: main product 277 mg (yield 58.7%) and by-product 70.2 mg (yield 14.9%).

WORKING EXAMPLE 44

3,4-Benzo-5-(2-pyrrolidon-1-yl)acethylamino-1-phenyl-2-oxabicyclo[4.1.0]heptane

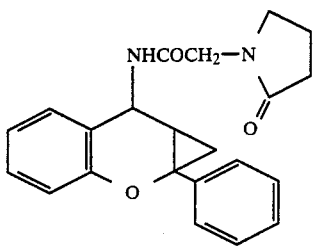

750 mg of the product obtained in Working Example 41 was dissolved in 50 ml of methylene chloride and 1.01 ml (4 equivalents) of chloroacetyl chloride and 2.66 ml of triethylamine were added to the solution. The mixture was heated with stirring for one hour and concentrated and the residue was purified by column chromatography on silica gel (methylene chloride:methanol 99:1) to obtain 854 mg of a chloroacetyl compound. This was heated with 260 mg (2.4 equivalents) of sodium hydride (as a 60% oil) and 0.248 ml (1.2 equivalents) of α-pyrrolidone in a solvent mixture of 30 ml of dioxane and 5 ml of dimethylsulfoxide at 110° C. for 3 hours. The reaction was treated in a manner similar to Working Example 22 to obtain 886 mg (yield 77.6%) of the titled compound.

WORKING EXAMPLE 45

3,4-Benzo-5-[(4-(2-pyrrolidon-1-yl)butyryl]amino-1-phenyl-2-oxabicyclo[4.1.0]heptane

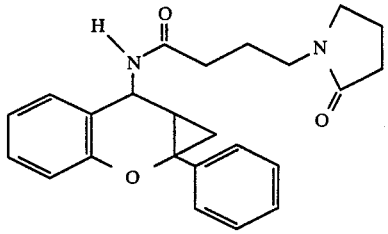

The product obtained in Working Example 41 was reacted with γ-chlorobutyryl chloride and the reaction was treated in a manner similar to Working Example 44 to obtain the titled compound (yield 54.7%).

WORKING EXAMPLE 46

3,4-Benzo-5-hydroxy-5-(4-dimethylaminobutyl)-1-phenyl-2-oxabicyclo[4.1.0]heptane

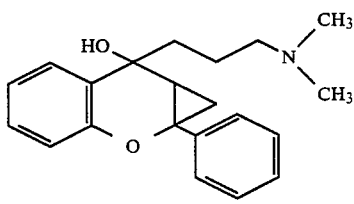

972 mg of magnesium and a catalytic amount of iodine were added to 30 ml of tetrahydrofuran and 2.31 g of dimethylaminopropyl chloride was added dropwise.

The mixture was heated to reflux for one hour. After cooling, 2.36 g of a solution of 3,4-benzo-5-oxo-1-phenyl-2-oxabicyclo[4.1.0]heptane in tetrahydrofuran was added dropwise to the mixture and stirred at room temperature for one hour. The reaction product was decomposed by adding a small amount of water and the tetrahydrofuran layer was separated. The aqueous layer was diluted with water and extracted with ether. The tetrahydrofuran solution and the ether extract were combined and washed with aqueous NaCl and dried over anhydrous magnesium sulfate. After filtration, the filtrate was concentrated and the residue was purified by column chromatography on silica gel (methylene chloride:methanol 90:10) to obtain 2.2 g (yield 69.6%) of the titled compound as a mixture of steric isomers.

The product was separated in the same manner as described above to obtain the main product and by-product in a ratio of 88:12.

Among the products obtained in the above examples, those whose melting points are not indicated are all oils. In Table 4, the physicochemical properties of the products obtained in the above Working Examples are given and the physicochemical properties of the products obtained in the above Reference Examples are given in Table 5.

The abbreviations given in the column for NMR spectrum in the Tables signify the following:
- s: singlet
- d: doublet
- t: triplet
- dd: doublet of doublet
- q: quartlet
- m: multiplet

TABLE 4

| Working Example No. | IR spectrum ($\nu$ cm$^{-1}$) | M.S. spectrum | NMR spectrum ($\delta$ ppm) |
|---|---|---|---|
| 1 | 1615, 1600 | Calculated: 322.1681 Found: 322.1708 | 1.62(t,1H), 1.87(dd,1H), 2.30(s,6H), 2.19(t,2H), 3.03(dd,1H), 4.30(m,1H), 6.95–7.85(m,9H) |
| 2 | 1615, 1600 | Calculated: 336.1838 Found: 336.1861 | 1.62(t,1H), 1.86–2.00 (m,3H), 2.49(t,1H), 3.01(dd,1H), 4.24(t,2H), 6.95–7.84(m,9H) |
| 3 | 1610, 1570 | Calculated: 336.1837 Found: 336.1847 | 1.53–1.66(m,2H), 1.84–2.00(m,2H), 2.26(s,6H), 2.42(t,2H), 2.53(d,1H), 4.12–4.28 (m,2H), 6.97–7.48(m,8H), 8.37(d,1H) |
| 4 | 1615, 1600 | 350(M$^+$)* 236 | 1.01(d,3H), 1.62(t,1H), 1.87(dd,1H), 2.10–2.30 (m,3H), 2.20(s,3H), 2.22(s,3H), 3.02(dd,1H), 3.96–4.04(m,1H), 4.16–4.24(m,1H), 6.95–7.84(m,9H) |
| 5 | 1620, 1610 | Calculated: 388.2149 Found: 388.2139 | 1.60(t,1H), 1.84–2.42 (m,10H), 2.51(t,1H), 2.86–2.96(m,2H), 3.22–3.30(m,3H), 3.75–3.84(m,1H), 4.31–4.41(m,1H), 6.91–7.83(m,9H) |
| 6 | 1660, 1640, 1620, 1600 | Calculated: 391.1893 Found: 391.1887 | 1.63(t,1H), 1.92(dd,1H), 2.26(s,3H), 2.35–2.40 (m,4H), 3.09(dd,1H), 3.52–3.57(m,2H), 3.62–3.68(m,2H), 4.85(s,2H), 6.94–7.82(m,9H) |
| 7 | 1615, 1600 | Calculated: 352.1785 Found: 352.1765 | 1.58(t,1H), 1.87(dd,1H), 2.32(s,6H), 2.70(t,2H), 2.98(dd,1H), 3.79(s,3H), 4.29(m,2H), 6.47–7.76(m,8H) |
| 8 | 1620, 1605 | Calculated: 356.1288 Found: 356.1271 | 1.58(t,1H), 1.89(dd,1H), 2.31(s,6H), 2.70(t,2H), 3.02(dd,1H), 4.30(m,2H), 6.95(dd,1H), 6.99(d,1H), 7.27–7.50(m,5H), 7.77(d,1H) |
| 9 | 1610, 1590 | 371(M$^+$)* | 1.59(t,1H), 1.86–2.03 (m,3H), 2.31(s,6H), 2.50(t,1H), 2.98(dd,1H), 4.24(t,1H), 6.95(dd,1H), 6.99(d,1H), 7.28–7.48 (m,5H), 7.75(d,1H) |
| 10 | 1615, 1560 | — | 1.58(t,1H), 1.83–1.96 (m,3H), 2.25(s,6H), 2.40(t,2H), 2.97(dd,1H), 4.20(m,2H), 5.03(s,2H), 6.54–7.76(m,13H) |
| 11 | 1610, 1595 | — | 1.65(t,1H), 1.85–1.96(m,3H), 2.24(s,6H), 2.41(t,2H), 3.06(dd,1H), 4.24(t,2H), 6.93–7.83(m,7H) |
| 12 | 1610, 1595 | Calculated: 415.1299 Found: 415.1304 | 1.73(t,1H), 1.95(m,3H), 2.24(s,5H), 2.38(t,2H), 3.08(dd,1H), 4.25(m,2H), 6.97(dd,1H), 7.03(d,1H), 7.55(d,2H), 7.77(d,1H), 8.25(d,2H) |
| 14 | 1620, 1600 | Calculated: 364.1785 Found: 364.1760 | 1.62(t,1H), 1.87(dd,1H), 2.52–2.57(m,4H), 2.76(t,2H), 3.00(dd,1H), 3.66–3.70(m,4H), 4.30–4.36(m,2H), 6.94–7.84(m,9H) |
| 15 | 1620, 1610 | Calculated: 322.1680 Found: 322.1680 | 1.61(t,1H), 1.88(dd,1H), 1.92–2.02(m,2H), 2.45(s,3H), 2.62(s,1H), 2.75(t,2H), 3.00(dd,1H), 4.27(t,2H), 6.94–7.85(m,9H) |
| 16 | 1615, 1600 | Calculated: 364.2148 Found: 364.2130 | 1.02(t,6H), 1.62(t,1H), 1.85–1.95(m,3H), 2.52–2.65(m,6H), 3.01(d,1H), 4.20–4.26 (m,2H), 6.95–7.84(m,9H) |
| 17 | 1620, 1610 | Calculated: 362.1991 Found: 362.1965 | 1.61(t,1H), 1.80–1.92 (m,5H), 2.02–2.12(m,2H), 2.67–2.76(m,6H), 2.99(dd,1H), 4.25(t,2H), 6.94–7.82(m,9H) |
| 18 | 1620, 1600 | Calculated: 412.2149 Found: 412.2134 | 1.59(t,1H), 1.84(dd,1H), 1.91–2.01(m,2H), 2.21(s,3H), 2.50(t,2H), 2.95(dd,1H), 3.50(s,2H), 4.26(t,2H), 6.92–7.84(m,14H) |
| 19 | 1610, 1600 | Calculated: 350.1992 Found: 350.1959 | 1.62(t,1H), 1.70–1.82 (m,4H), 1.87(dd,1H), 2.23(s,6H), 2.32(t,2H), 3.01(dd,1H), 4.20(t,2H), 6.92–7.84(m,9H) |
| 20 | 1620, 1605 | Calculated: 336.1836 Found: 336.1821 | 1.61(t,1H), 1.72–2.12 (m,5H), 2.60(s,3H), 2.98(m,3H), 4.19(t,2H), 6.97(m,2H), 7.24–7.52 (m,6H), 7.80(d,1H) |
| 21 | 1615, 1610 | Calculated: 364.2148 Found: 364.2145 | 1.37–1.82(m,7H), 1.88(dd,1H), 2.21(s,6H), 2.27(t,2H), 3.02(dd,1H), 4.18(t,2H), 6.94–7.84(m,9H) |
| 22 | 1690, 1680, 1615, 1600 | Calculated: 376.1884 Found: 376.1763 | 1.62(t,1H), 1.82–2.04 (m,5H), 2.36(t,2H), 3.01(dd,1H), 3.37–3.44 (m,4H), 4.22(t,2H), 6.95–7.83(m,9H) |

TABLE 4-continued

| Working Example No. | IR spectrum ($\nu$ cm$^{-1}$) | M.S. spectrum | NMR spectrum ($\delta$ ppm) |
|---|---|---|---|
| 23 | 1600, 1580 | Calculated: 310.1804 Found: 310.1799 | 1.37(dd,1H), 1.58(t,1H), 2.10-2.17(m,1H), 2.36(s,6H), 2.69(t,2H), 3.73-3.82(m,1H), 3.92-4.00(m,1H), 4.95(d,1H), 6.94-7.55(m,9H) |
| 24 | 1610, 1585 | Calculated: 323.1884 Found: 323.1844 | 1.34(d,1H), 1.57(t,1H), 1.84-1.95(m,2H), 2.10-2.17(m,1H), 2.27(s,6H), 2.44-2.49(m,2H), 3.66-3.73(m,1H), 3.86-3.95(m,1H), 4.90(d,1H), 6.93-7.54(m,9H) |
| 25 | 1660, 1650, 1620, 1590 | Calculated: 378.1944 Found: 378.1979 | 1.38(dd,1H), 1.55(t,1H), 2.18(dd,1H), 2.32(s,3H), 2.40-2.48(m,4H), 3.60-3.72(m,4H), 4.45(s,2H), 5.06(d,1H), 6.96-7.57(m,9H) |
| 26 | 1605, 1580 | Calculated: 343.1336 Found: 343.1335 | 1.38(dd,1H), 1.54(t,1H), 2.13(m,1H), 2.34(s,6H), 2.66(t,2H), 3.76(m,1H), 3.93(m,1H), 4.89(d,1H), 6.99(m,2H), 7.24-7.52(m,6H) |
| 27 | 1605, 1575 | Calculated: 357.1496 Found: 357.1498 | 1.36(dd,1H), 1.52(t,1H), 1.90(m,2H), 2.15(m,1H), 2.27(s,6H), 2.43(m,2H), 3.68(m,1H), 3.88(m,1H), 4.84(d,1H), 6.96(m,2H), 7.25-7.50(m,6H) |
| 28 | 1615, 1580 | Calculated: 339.1833 Found: 339.1813 | 1.36(dd,1H), 1.53(t,1H), 2.04-2.13(m,1H), 2.36(s,6H), 2.69(t,2H), 3.70-3.85(m,1H), 3.77(s,3H), 3.92-3.98(m,1H), 4.88(d,1H), 6.46-7.43(m,8H) |
| 29 | 1620, 1580 | — | 1.35(dd,1H), 1.54(t,1H), 1.86-1.96(m,2H), 2.05-2.13(m,1H), 2.28(s,6H), 2.47-2.54(m,2H), 3.67(d,t,1H), 3.88(d,t,1H), 4.85(d,1H), 5.04(s,2H), 6.57-7.46(m,13H) |
| 30 | 1615, 1590 | Calculated: 337.2040 Found: 337.2040 | 1.28-1.38(m,1H), 1.56(t,1H), 1.65-1.80(m,4H), 2.08-2.17(m,1H), 2.23(s,6H), 2.32(t,2H), 3.62-3.70(m,1H), 3.83-3.92(m,1H), 4.88(d,1H), 6.93-7.53(m,9H) |
| 31 | 1610, 1580 | Calculated: 365.2352 Found: 365.2344 | 1.32-1.37(m,1H), 1.42-1.93(m,9H), 2.08-2.17(m,1H), 2.72(s,6H), 2.88-2.95(m,2H), 3.59-3.67(m,1H), 3.82-3.90(m,1H), 4.88(d,1H), 6.94-7.51(m,9H) |
| 32 | 1620, 1580 | — | 1.35(dd,1H), 1.54(t,1H), 1.65-1.76(m,4H), 2.03-2.13(m,1H), 2.30(s,6H), 2.39(t,2H), 3.58-3.67(m,1H), 3.81-3.89(m,1H), 4.83(d,1H), 5.02(s,2H), 6.57-7.44(m,13H) |
| 33 | 1695, 1680, 1610, 1580 | Calculated: 377.1991 Found: 377.2006 | 1.35(dd,1H), 1.55(t,1H), 1.70-2.17(m,7H), 2.40(t,2H), 3.32-3.42(m,4H), 3.62-3.70(m,1H), 3.84-3.93(m,1H), 4.89(d,1H), 6.94-7.51(m,9H) |
| 34 | 3350, 1610, 1595 | 352(M$^+$)* | 1.54(t,1H), 1.82(dd,1H), 1.94-2.04(m,2H), 2.28(s,6H), 2.47-2.57(m,2H), 2.91(dd,1H), 4.12-4.22(m,2H), 6.34-7.53(m,8H) |
| 35 | 3300, 1620, 1600 | Calculated: 339.1832 Found: 339.1800 | 1.28(dd,1H), 1.43(t,1H), 1.94-2.12(m,1H), 2.59(s,6H), 2.92-2.98(m,2H), 3.58-3.66(m,1H), 3.80-3.86(m,1H), 4.74(d,1H), 6.40-7.47(m,8H) |
| 36 | 3400, 1620, 1585 | — | 1.28(dd,1H), 1.47(t,1H), 1.64-1.80(m,4H), 1.96-2.02(m,1H), 2.36(s,6H), 2.47-2.52(m,2H), 3.56-3.61(m,1H), 3.76-3.85(m,1H), 4.75(d,1H), 6.38-7.40(m,8H) |
| 37 | 1770, 1620, 1605 | Calculated: 395.1969 Found: 395.1929 | 1.63(t,1H), 1.90(dd,1H), 1.96-2.06(m,2H), 2.28(s,3H), 2.34(s,6H), 2.58(t,2H), 2.97(dd,1H), 4.22(t,2H), 6.70-7.85(m,8H) |
| 38 | 1760, 1615, 1590 | Calculated: 381.1939 Found: 381.1989 | 1.37(dd,1H), 1.53(t,1H), 1.91-2.01(m,2H), 2.08-2.17(m,1H), 2.27(s,3H), 2.37(s,6H), 2.57-2.63(m,2H), 3.66-3.73(m,1H), 3.87-3.95(m,1H), 4.86(d,1H), 6.72-7.52(m,8H) |
| 39 | 1735, 1625, 1610 | 423(M$^+$)* 323 | 1.63(t,1H), 1.92(dd,1H), 2.23-2.34(m,2H), 2.72(s,6H), 2.93(dd,1H), 2.98(s,3H), 3.08(s,3H), 3.03-3.10(m,2H), 4.27(t,2H), 6.74-7.78(m,8H) |
| 40 | 1690, 1620 | Calculated: 410.2077 Found: 410.2072 | 1.58(t,1H), 1.86-1.98(m,3H), 2.26(s,6H), 2.42(t,2H), 3.00(dd,1H), 4.22(t,2H), 4.48(s,2H), 5.90(s,2H), 6.48-7.80(m,8H) |
| 41 | 3300, 1600, 1580 | Calculated: 237.1151 Found: 237.1124 | 1.20(dd,1H), 1.39(t,1H), 1.82-1.88(m,1H), 4.39(d,1H), 6.92-7.58(m,9H) |
| 42 | 3300, 1700, 1610, 1590 | — | 1.18-1.46(m,6H), 1.94-2.01(m,1H), 4.12(q,2H), 4.94-5.03(m,1H), 5.32(d,1H), 6.92-7.47(m,9H) |
| 43 Main product | 1610, 1585 | Calculated: 265.1467 Found: 265.1451 | 1.26-1.33(m,1H), 1.54(t,1H), 1.87-1.96(m,1H), 2.45(s,6H), 4.28(d,1H), 6.92-7.68(m,9H) |
| 43 By-product | 1600, 1580 | Calculated: 265.1467 Found: 265.1469 | 1.20(dd,1H), 1.38(t,1H), 1.78-1.86(m,1H), 2.22(s,6H), 4.30(s,1H), 6.92-7.47(m,9H) |
| 44 | 3250, 1690, 1660, 1600, 1580 | Calculated: 362.1628 Found: 362.1613 | 1.22-2.44(m,7H), 3.36-3.42(m,2H), 3.83(d,1H), 3.92(d,1H), 5.64(dd,1H), 6.73(d,1H), 6.94-7.46(m,9H) |
| 45 | 3350, 1690, 1610, 1580 | — | 1.32(m,1H), 1.49(t,1H), 1.57-1.70(m,4H), 1.75-1.97(m,3H), 2.12(m,1H), 2.37(m,2H), 2.57(m,1H), 2.90(m,1H), 3.30(m,1H), 5.89(s,1H), 6.90-7.50(m,9H) |
| 46 Main product | 3350, 1600, 1575 | — | 1.20(dd,1H), 1.50(t,1H), 1.70(m,2H), 2.04(m,3H), 2.52(s,6H), 2.73(m,2H), 4.20(s,1H), 6.87-7.75(m,9H) |
| 46 By-product | 3350, 1605, 1580 | — | 1.17(dd,1H), 1.49(m,3H), 1.93(m,3H), 2.30(s,6H), 2.35(t,2H), 5.44(s,1H), |

TABLE 4-continued

| Working Example No. | IR spectrum ($\nu$ cm$^{-1}$) | M.S. spectrum | NMR spectrum ($\delta$ ppm) |
|---|---|---|---|
| | | | 6.83–7.64(m,9H) |

*Value determined by low resolution mass spectrum

TABLE 5

| Reference example No. | IR spectrum ($\nu$ cm$^{-1}$) | NMR spectrum ($\delta$ ppm) |
|---|---|---|
| 1 Compound IIIc | 3300 1640 1600 | 1.65(t,1H), 1.93(dd,1H), 3.13(dd,1H), 6.96–7.79(m,9H), 8.62(s,1H) |
| 1 Compound IIId | 3200 1600 | 1.57(t,1H), 1.65(dd,1H), 2.53(dd,1H), 7.00–8.47(m,9H) |
| 2 | 3200, 1620 1615, 1605 | 1.62(t,1H), 1.91(dd,1H), 3.09(dd,1H), 3.80(s,3H), 6.49–7.70(m,8H), 8.62(m,1H) |
| 3 | 3200 1640 1600 1560 | 1.61(dd,1H), 1.94(dd,1H), 3.11(dd,1H), 6.96(dd,1H), 7.02(d,1H), 7.28–7.50(m,5H), 7.70(d,1H), 7.99(s,1H) |
| 4 | 3400 1610 1570 | 1.62(t,1H), 1.91(dd,1H), 3.07(dd,1H), 5.04(s,2H), 6.57–7.72(m,13H) |
| 5 | 3250, 1645 1605, 1575 | 1.62(t,1H), 1.90(dd,1H), 3.17(dd,1H), 6.77–7.78(m,7H), 9.08(s,1H) |
| 6 | 3200 1600 1560 | 1.77(t,1H), 1.99(dd,1H), 3.19(dd,1H), 6.99(dd,1H), 7.07(d,1H), 7.57(d,2H), 7.72(d,1H), 8.27(d,2H) |
| 7 | 1620 1610 | 1.62(t,1H), 1.88(dd,1H), 3.06(dd,1H), 3.62(t,2H), 4.46(t,2H), 6.93–7.82(m,9H) |
| 8 | 1620 | 1.61(t,1H), 1.88(dd,1H), 2.16–2.26(m,2H), 2.98(dd,1H), 3.67(t,2H), 4.30–4.36(m,2H), 6.93–7.83(m,9H) |
| 9 | 1615 1600 | 1.51(t,1H), 1.84–2.06(m,5H), 2.99(dd,1H), 3.47(t,2H), 4.22(t,2H), 6.95–7.83(m,9H) |
| 10 | 1610 1595 | 1.60–1.98(m,8H), 3.01(dd,1H), 3.42(t,2H), 4.20(t,2H), 6.94–7.85(m,9H) |
| 11 | 3350 1605 1580 | 1.25–1.35(m,1H), 1.47–1.54(m,1H), 1.90(d,1H), 2.04–2.23(m,1H), 5.17–5.25(m,1H), 6.94–7.63(m,9H) |
| 12 | — | 1.30(dd,1H), 1.48(t,1H), 1.94(d,1H), 2.20(m,1H), 5.15(dd,1H), 6.95(m,2H), 7.22–7.50(m,5H), 7.54(d,1H) |
| 13 | 3350 1610 1590 | 1.29(dd,1H), 1.48(t,1H), 1.86(dd,1H), 2.13–2.22(m,1H), 3.78(s,3H), 5.14(dd,1H), 6.49–7.50(m,8H) |
| 14 | 3350 1620 1590 | 1.28(dd,1H), 1.48(t,1H), 1.88(d,1H), 2.13–2.21(m,1H), 5.02(s,2H), 5.14(dd,1H), 6.56–7.50(m,13H) |
| 15 | 1610 1590 | 1.25–2.27(m,7H), 3.50(t,2H), 3.63–3.72(m,1H), 3.85–3.95(m,1H), 4.90(d,1H), 6.92–7.50(m,9H) |
| 16 | 1610 1580 | 1.32–1.38(m,1H), 1.52–1.95(m,9H), 2.08–2.17(m,1H), 3.46(t,2H), 3.61–3.69(m,1H), 3.82–3.90(m,1H), 4.98(d,1H), 6.93–7.53(m,9H) |
| 17 | 1625 1595 | 1.36(m,1H), 1.71(m,1H), 1.94(m,1H), 2.00–2.13(m,4H), 3.40–3.52(m,2H), 3.61–3.67(m,1H), 3.83–3.90(m,1H), 4.84(d,1H), 5.03(s,2H), 6.56–7.44(m,13H) |

What is claimed is:

1. An oxabicycloheptane derivative having the following general formula or a pharmaceutically acceptable salt thereof:

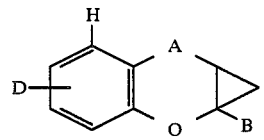

where D is a hydrogen atom, a halogen atom, a hydroxyl group, an alkoxy group, an arylalkoxy group, an acyloxy group, a dialkylcarbamoyloxy group or an amidoalkyloxy group; B is a substituted or unsubstituted phenyl, thienyl or furyl group; ⟋A⟍ is the group

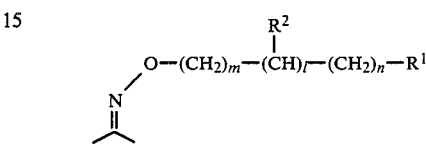

(where l is 0 or 1; m and n are each 1 or more, provided that m+n is an integer of 2–8; $R^1$ is an alkylamino group, a dialkylamino group, an arylalkylamino group, a morpholino group, a thiomorpholino group, a 1-pyrrolidinyl group, a piperidino group, an N-alkylpiperazinyl group, an N-hydroxyalkylpiperazinyl or a pyrrolizidinyl group; and $R^2$ is a lower alkyl group or a hydroxyl group), or the group

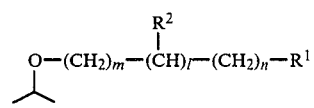

(where l, m, n, $R^1$ and $R^2$ are each the same as defined above), or the group

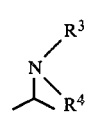

(where $R^3$ and $R^4$ which may be the same or different each represents a hydrogen atom, a lower alkyl group, an alkoxycarbonyl group or an acyl group), or the group

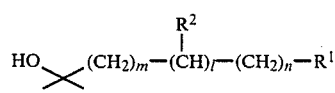

(where m, l, n, $R^1$ and $R^2$ are each the same as defined above).

2. A compound according to claim 1 wherein B is a phenyl group, a halogenophenyl group, a nitrophenyl group, a thienyl group, a halogenothienyl group, a nitrothienyl group, a furyl group, a halogenofuryl group or a nitrofuryl group.

3. A compound according to claim 1 wherein $R^1$ is an alkylamino or dialkylamino group having an alkyl group with 1–4 carbon atoms, an arylalkylamino group having 7–9 carbon atoms, an alkyl-arylalkylamino group having both an alkyl group with 1–4 carbon atoms and an arylalkyl group with 7–9 carbon atoms, a morpholino group, a thiomorpholino group, a 1-pyrrolidinyl group, a 2-oxo-1-pyrrolidinyl group, a piperidino group, an N-alkylpiperazinyl group having 5-7 carbon atoms, an N-hydroxyalkylpiperazinyl group having an alkyl group with 1-3 carbon atoms, or a pyrrolizidinyl group.

4. A compound according to claim 1 wherein $R^3$ and $R^4$ which may be the same or different each represents a hydrogen atom, an alkyl group having 1-3 carbon atoms, or an alkoxycarbonyl group having 2-5 carbon atoms or pyrrolidonylalkylcarbonyl group having 5-10 carbon atoms.

5. A compound according to claim 1 wherein D is a hydrogen atom, a chlorine atom, a bromine atom, a fluorine atom, a hydroxyl group, a methoxy group, an ethoxy group, a propyloxy group, a butyloxy group, a benzyloxy group, an acetyloxy group, a propionyloxy group, a butyryloxy group, a dimethylcarbamoyloxy group, a diethylcarbamoyloxy group, a diisopropylcarbamoyloxy group, an amidomethyloxy group, an aminoethyloxy group, or an amidoethylpropyloxy group.

\* \* \* \* \*